(12) United States Patent
Jones

(10) Patent No.: US 10,265,482 B2
(45) Date of Patent: Apr. 23, 2019

(54) NEEDLE-POINT PEN APPARATUS, METHODS, AND SYSTEMS FOR ADMINISTERING MEDICATION

(71) Applicant: SOUL SKINS LLC, Salt Lake City, UT (US)

(72) Inventor: David Allan Jones, Salt Lake City, UT (US)

(73) Assignee: SOUL SKINS LLC, Salt Lake City, UT (US)

( * ) Notice: Subject to any disclaimer, the term of this patent is extended or adjusted under 35 U.S.C. 154(b) by 755 days.

(21) Appl. No.: 14/872,167

(22) Filed: Oct. 1, 2015

(65) Prior Publication Data

US 2016/0067739 A1 Mar. 10, 2016

(51) Int. Cl.
*A61M 5/32* (2006.01)
*A61M 5/46* (2006.01)
(Continued)

(52) U.S. Cl.
CPC .......... *A61M 5/3287* (2013.01); *A61M 5/158* (2013.01); *A61M 5/32* (2013.01);
(Continued)

(58) Field of Classification Search
CPC .. A61M 2005/1583; A61M 2005/1585; A61M 5/3287; A61M 5/46; A61M 2205/50; A61M 5/142; A61M 5/145; A61M 5/158; A61M 5/3129; A61M 5/32; A61M 5/3295; A61M 5/3298; A61M 5/34; A61M 2005/1586; A61M 2005/3289;
(Continued)

(56) References Cited

U.S. PATENT DOCUMENTS 180,857 A 8/1876 Ta Edison
196,747 A 11/1877 Ta Edison
(Continued)

FOREIGN PATENT DOCUMENTS

WO WO2015038072 3/2015

OTHER PUBLICATIONS

Ballpoint pen—Wikipedia, the free encyclopedia (Oct. 22, 2015).
(Continued)

*Primary Examiner* — Shefali D Patel
(74) *Attorney, Agent, or Firm* — Alpine IP PLLC; David A Jones

(57) ABSTRACT

A needle-point pen apparatus and methods for administering a medication. The needle-point pen apparatus can include a barrel, a needle movably disposed within an inner channel of the barrel, the needle having a tip and an elongate shaft. A driving unit is coupled to the needle and provides a driving actuation to the needle. The driving actuation causes the needle to reciprocate within the barrel between one or more extended and retracted positions. The needle being designed to at least partially insert the medication into living tissue. A medication reservoir supplies the medication to the needle for at least partial insertion into the tissue. A computing device controls the needle actuation and the supply of the medication to the needle for controlling administration of the medication at multiple different computer-controlled depths and/or locations of the tissue.

20 Claims, 13 Drawing Sheets

(51) Int. Cl.
*A61M 5/158* (2006.01)
*B27K 3/02* (2006.01)
*G05B 19/19* (2006.01)
*C14C 11/00* (2006.01)
*H05K 3/12* (2006.01)
*C14B 5/00* (2006.01)
*D06H 1/02* (2006.01)

(52) U.S. Cl.
CPC ........ *A61M 5/3295* (2013.01); *A61M 5/3298* (2013.01); *A61M 5/46* (2013.01); *A61M 2005/1583* (2013.01); *A61M 2005/1585* (2013.01); *A61M 2205/50* (2013.01); *B27K 3/025* (2013.01); *C14B 5/00* (2013.01); *C14C 11/00* (2013.01); *D06H 1/02* (2013.01); *G05B 19/19* (2013.01); *G05B 2219/45134* (2013.01); *H05K 3/12* (2013.01); *Y02P 80/40* (2015.11)

(58) Field of Classification Search
CPC ........ A61M 2005/341; A61M 37/0076; A61M 37/0084; A61M 2205/3331
See application file for complete search history.

(56) References Cited

U.S. PATENT DOCUMENTS

| | | | |
|---|---|---|---|
| 4,245,260 A | 1/1981 | Doelves | |
| 5,823,993 A * | 10/1998 | Lemelson | G01R 33/561 |
| | | | 604/503 |
| 7,518,479 B2 | 4/2009 | Mask et al. | |
| 8,377,034 B2 * | 2/2013 | Tallarida | A61M 39/0208 |
| | | | 604/513 |
| 8,690,832 B2 * | 4/2014 | Racz | A61M 5/3291 |
| | | | 604/164.07 |
| 2004/0220536 A1 * | 11/2004 | VanTassel | A61M 5/3286 |
| | | | 604/272 |
| 2005/0028647 A1 | 2/2005 | Sloan | |
| 2008/0312604 A1 * | 12/2008 | Boesen | A61M 5/008 |
| | | | 604/207 |
| 2009/0149812 A1 * | 6/2009 | MacAulay | A61M 5/427 |
| | | | 604/117 |
| 2013/0125319 A1 | 5/2013 | Regan | |
| 2014/0324089 A1 * | 10/2014 | Chan | A61M 37/0076 |
| | | | 606/185 |

OTHER PUBLICATIONS

Pen Needles—Wikipedia, the free encyclopedia (Oct. 22, 2015).
Stippling—Wikipedia, the free encyclopedia (Oct. 22, 2015).
Oscillation—Wikipedia, the free encyclopedia (Oct. 22, 2015).
Hatching—Wikipedia, the free encyclopedia (Oct. 22, 2015).
Joint Replacment—Wikipedia, the free encyclopedia (Oct. 22, 2015).
Stephen Biesty—Wikipedia, the free encyclopedia (Oct. 22, 2015).
Tattoo Machine—Wikipedia, the free encyclopedia (Oct. 22, 2015).
Electronic Oscillator—Wikipedia, the free encyclopedia (Oct.22, 2015).

* cited by examiner

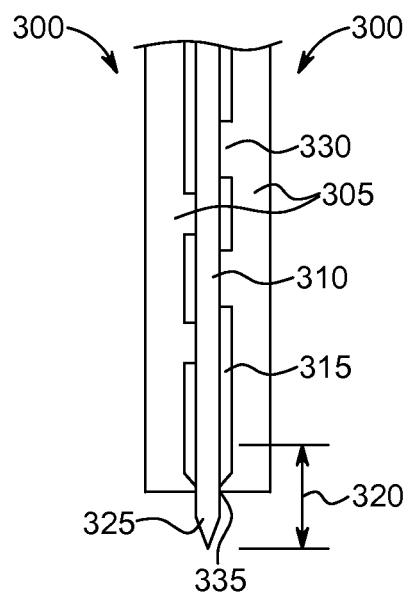
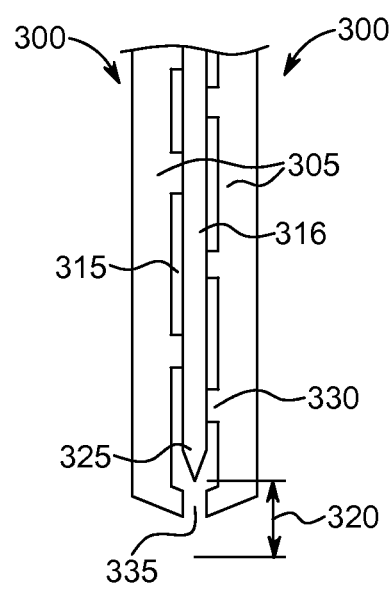
FIG. 3A          FIG. 3B
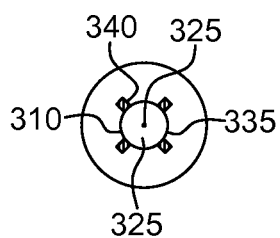
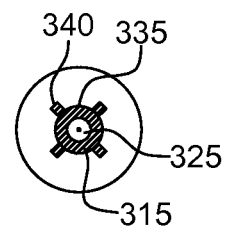
FIG. 3C          FIG. 3D

NEEDLE-POINT PEN APPARATUS, METHODS, AND SYSTEMS FOR ADMINISTERING MEDICATION

BACKGROUND

Examples of marking tools include pencils, Crayons, brushes, engravers, rollers, chisels, pens, chalk, stacks of rocks, grinders, welders, branding, wearable marks/indicia, etc. Virtual marking devices include computer mice, keyboards, stylus, and touch pads often in connection with software and electronic digital models and images of tangible articles and maps, or topographic models, as well as virtual marking, manufacturing, meta-code, and image/model versions and revisions. Image and digital models of shoes, bones, clothing, etc. include computer-based modeling software in connection with digital models, such as point clouds and artistic designs, which can be transformed to a tangible use or involved with digital and real-life creation of objects and products.

A three dimensional model of any tangible real-life object can be created. Attributes of that object can be assigned to image pixels, surfaces, and real-life characteristics. A bone may be brittle, a plant may fluoresce chlorophyll, and art and roller-coasters may be appreciated. And, new tools are created for quantifying, improving, and enhancing objects' attributes.

Electronic, mechanical, and computer-related machines are also used to control electro-mechanical marking and manufacturing tools. Examples of marking acts include painting, engraving, etching (e.g. cutting), chemical reacting, curing, branding, dying, stamping, covering, replacing, scarring, material deposition or material connection, treatment, scratching, hiding, deforming, bending, and/or other means of marking and manufacturing objects.

Material removal marking has also been used. For example, chisels have been used to remove material in a marking and/or manufacturing process. Clay has been used to form and make pottery. Clay can be dyed and cured. And, subsequently, a chisel or engraver can be used to remove cured and dyed clay to again expose the underlying undyed clay and its characteristics. Then, once again, a dye, ink, or paint can be further applied to the newly exposed clay and/or previously dyed clay, if desired. Features, such as a handle for holding a clay pot, may also be added to the pottery or a handle may be created by removing part of the pottery to create the handle.

Referring to FIG. 1, a conventional ball-point pen 100 marking instrument is illustrated. The ballpoint pen 100, also known as a "biro" and "ball-point pen", is a pen that dispenses ink over a metal ball at its point, i.e. over a "ball point". The metal commonly used is steel, brass, or tungsten carbide. It was conceived and developed as a cleaner and more reliable alternative to quill and fountain pens, and it is now the world's most-used writing instrument: millions are manufactured and sold daily. As a result, it has influenced art and graphic design and spawned an artwork genre.

The concept of using a ball point within a writing instrument as a method of applying ink to paper has existed since the late 19th century. In these inventions, the ink 115 was placed in a thin tube 120 whose end was blocked by a tiny ball 110, held so that it could not slip into the tube 120 or fall out of the pen 100. The ink 115 clung to the ball 110, which spun as the pen 100 was drawn across the paper 125 or other material, therefore giving areas of the ball 110 with its ink 115 transferred to the paper 125 allowing for another (or continued) coating of ink 110.

The first patent for a ballpoint pen was issued on 30 Oct. 1888, to John J. Loud, who was attempting to make a writing instrument that would be able to write "on rough surfaces-such as wood, coarse wrapping-paper, and other articles" which then-common fountain pens could not. Loud's pen had a small rotating steel ball, held in place by a socket. Although it could be used to mark rough surfaces such as leather, as Loud intended, it proved to be too coarse for letter-writing. With no commercial viability, its potential went unexploited and the patent eventually lapsed. The manufacture of economical, reliable ballpoint pens as we know them today arose from experimentation, modern chemistry, and precision manufacturing capabilities of the early 20th century. Patents filed worldwide during early development are testaments to failed attempts at making the pens commercially viable and widely available. Early ballpoints did not deliver the ink evenly; overflow and clogging were among the obstacles inventors faced toward developing reliable ballpoint pens. If the ball socket were too tight, or the ink too thick, it would not reach the paper. If the socket were too loose, or the ink too thin, the pen would leak or the ink would smear. Ink reservoirs pressurized by piston, spring, capillary action, and gravity would all serve as solutions to ink-delivery, ink pressure, and flow problems.

Laszlo Biro, a Hungarian newspaper editor frustrated by the amount of time that he wasted filling up fountain pens and cleaning up smudged pages, noticed that inks' characteristics used in newspaper printing dried quickly, leaving the paper dry and smudge free. He decided to create a pen using the same type of ink. Biro enlisted the help of his brother Gyorgy, a chemist, to develop viscous ink formulas/chemistries for new ballpoint designs.

Biro's innovation successfully coupled ink-viscosity with a ball-socket mechanism which act compatibly to prevent ink from drying inside the reservoir while allowing controlled flow. Biro filed a British patent on Jun. 15, 1938.

In 1941, the Biro brothers and a friend, Juan Jorge Meyne, fled Germany and moved to Argentina, where they formed Biro Pens of Argentina and filed a new patent in 1943. Their pen was sold in Argentina as the Birome, which is how ballpoint pens are still known in that country. This new design was licensed by the British, who produced ballpoint pens for RAF aircrew as the Biro. Ballpoint pens were found to be more versatile than fountain pens, especially at high altitudes, where fountain pens were prone to ink-leakage.

A tattoo machine, in comparison, is a hand-held device generally used to create a tattoo, a permanent marking of the skin with indelible ink. Modern tattoo machines use electromagnetic coils to move an armature bar up and down. Connected to the armature bar is a barred needle grouping that pushes ink into the living skin. Tattoo artists generally use the term "machine", or even "iron", to refer to their equipment. There are also rotary tattoo machines, which are powered by regulated motors rather than electromagnetic coils.

The predecessor to the tattoo machine was the electric pen invented by Thomas Edison and patented under the title "Improvement in Stencil-Pens" in Newark, N.J., United States in 1877. It was originally intended to be used as a duplicating device, but in 1891, Samuel O'Reilly discovered that Edison's machine could be modified and used to introduce ink into the skin.

Tattoo inks are generally composed of pigments or dyes combined with a tattoo pigment vehicle which entraps, encases, incorporates, complexes, encapsulates, or is otherwise associated with the pigment to form pigment/vehicle complexes that retain the pigment in the living skin.

Leather crafting or simply leathercraft is the practice of making leather into craft objects or works of art, using shaping techniques, coloring techniques or both.

Leather dyeing usually involves the use of spirit- or alcohol-based dyes where alcohol quickly gets absorbed into moistened leather, carrying the pigment deep into the surface. "Hi-liters" and "Antiquing" stains can be used to add more definition to patterns. These have pigments that will break away from the higher points of a tooled piece and so pooling in the background areas give nice contrasts. Leaving parts unstained also provides a type of contrast.

Leather painting differs from leather dyeing in that paint remains only on the surface while dyes are absorbed into the leather. Due to this difference, leather painting techniques are generally not used on items that can or must bend nor on items that receive friction, such as belts and wallets because under these conditions, the paint is likely to crack and flake off. However, latex paints can be used to paint such flexible leather items. In the main though, a flat piece of leather, backed with a stiff board is ideal and common, though three-dimensional forms are possible so long as the painted surface remains secured.

Acrylic paint is a common medium, often painted on tooled leather pictures, backed with wood or cardboard, and then framed. Unlike photographs, leather paintings are displayed without a glass cover, to prevent mold.

Leather carving entails using metal implements to compress moistened leather in such a way as to give a three-dimensional appearance to a two-dimensional surface. The surface of the leather is not intended to be cut through, as would be done in filigree.

The main tools used to "carve" leather include: swivel knife, veiner, beveler, pear shader, seeder, cam, and background tool. The swivel knife is held similar to pencil and drawn along the leather to outline patterns. The other tools are punch-type implements struck with a wooden, nylon or rawhide mallet. The object is to add further definition with them to the cut lines made by the swivel knife.

Methods and machines for decorating, manufacturing and/or assembling a wearable leather article are also known. Examples of wearable leather articles include shoes, hats, pants, and jackets. Methods and machines for decorating, manufacturing and/or assembling a leather furniture articles are also known. Examples of leather furniture articles include cushions of chairs, seats, sofas, and stools. And, other leather accessories such as bags, totes, covers, cases, etc. have been made and decorated.

As disclosed herein, certain embodiments disclosed herein relate to needle-point pen utensils for marking tangible articles. Other features, tools, and newly discovered benefits are further discussed hereinafter in the Detailed Description or would be understood to one of ordinary skill in the art in view of the newly discovered and disclosed tools, methods, processes, control, and benefits discussed herein.

BRIEF DESCRIPTION OF THE DRAWINGS

FIGS. 1, 2, 3A, 3B, 3C, 3D, 4, 5, 6, 7, 8, 9, 10A, and 10B illustrate various needle-point pen designs according to example embodiments of the present invention;

DESCRIPTION OF EXAMPLE EMBODIMENTS ILLUSTRATING THE INVENTION

The embodiments discussed in this description are illustrative of needle-point pen apparatuses and methods for marking and/or creating articles and objects. Other uses for the needle-point pen are also disclosed hereinafter including medical, data storage, and identification. Further needle, ink, and positioning carriage control improvements are further discussed as well as marking and manufacturing processes and further control, characterization and design parameters, components, and processes.

Figure 1:
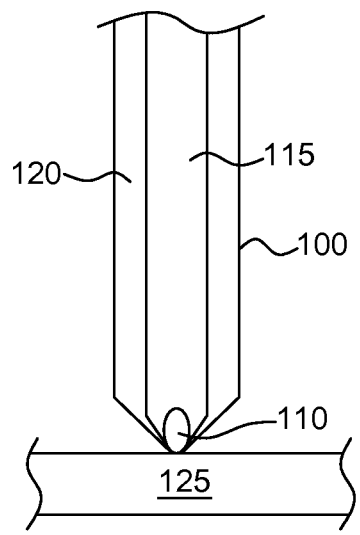
Figure 2:
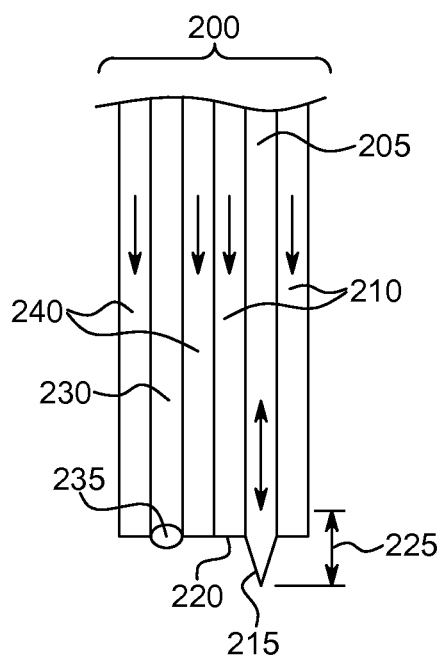

FIG. 2 illustrates a needle-point pen 200 according to one embodiment. This needle-point pen 200 includes a needle 205 that linearly reciprocates or oscillates within a barrel 210. The barrel 210 is a guiding support for the needle 205 to oscillate along a length of the barrel 210 and/or within the barrel 210 as shown. A cross-sectional shape of the barrel 210 can correspond to a cross-sectional shape (e.g. circular, elliptical, and/or square) of the needle 205. As shown, the needle 205 can also have a length such that oscillation of the needle 205 extends a distal end (or point) 215 of the needle 205 past a distal end 220 of the barrel 210. The end 215 of the needle 205 that extends beyond the end 220 of the barrel 210 can be angled relative to a direction of reciprocation, include a contact tip and/or be relatively sharp or relatively dull as compared to another needle.

A distance of reciprocation 225 of the needle 210 can be described by a stroke 225 of the needle 205. The stroke 225 of the needle 205 can be associated with a translational oscillation amplitude. This stroke 225 can describe a distance between a location of the end 215 of the needle 205 at a retracted position and a location of the end 215 of the needle 205 at an extended position. The extended position can be a "fully" extended position and the retracted position can be a "fully" retracted position to which partially extended and partially retracted positions ("fuzzy positions" or "intermediate positions") may be defined there between.

An oscillation of the needle 205 can be a repetitive variation, e.g. in time, of some measure about a central value (often a point of equilibrium) or between two or more different states (e.g. an extended position and a retracted position of the needle 205). The term 'vibration' is used to describe mechanical oscillation but used as a synonym of 'oscillation' too but may be defined by extent of movement of the needle 205. Familiar examples include a swinging pendulum and alternating current power. Oscillations occur not only in mechanical systems but also in dynamic systems. Thus, the oscillation of a needle-tip pen 200 can deal with the quantification of the amount that a sequence or function tends to move between extremes, which extremes can be modified, controlled, predetermined, and/or defined according to a stored parameter and/or executable computer instruction using control parameters as inputs.

In addition, an oscillating system may be subject to some external force, as when an AC circuit is connected to an outside power source. In this case the oscillation is said to be "driven".

An electronic oscillator is an electronic circuit that produces a periodic, oscillating electronic signal, often a sine wave, jagged, or a square wave. Oscillators convert direct current (DC) from a power supply to an alternating current signal. Examples of signals generated by oscillators include signals broadcast by radio and television transmitters, clock signals that regulate computers and quartz clocks, and the sounds produced by electronic beepers and video games. As discussed herein, the oscillation of a needle-tip pen can be controlled according to an oscillation form (or force component form) that can define needle tip position, imprint needle depth, a force level/amplitude or other time-based quantity profile. Thus, the motion and/or force applied to a needle and needle tip of a pen element can be controlled in-time, position, angle and force/actuation. Similarly, an ink, liquid application, and/or dye associated with such needle instrument can also be controlled according to pressure, volume, flow, attribute such as colour intensity and/or chemistry by the needle tip pen or subsequent to application by the needle tip pen during a curing process.

The needle tip, or needle-point, can also be a contact tip for contacting a material. Contact with the material can occur in-between the retracted position of the needle and the extended position of the needle. The position of the needle contact with the material can be referred to as the contact point of extension. And, the distance of penetration of the needle tip into the material in between the contact point and the extended point can describe a penetration depth of the needle (or contact tip of the needle) into the material.

In addition to the penetration depth, the needle penetration into the material can be defined by other characteristics of the needle including needle tip-shape and adjacent (or previous in-time and location considered) needle penetration characteristics. Tip characteristics can include how sharp or dull the needle tip is. Tip characteristics can include a taper angle of the needle tip, or a taper shape (e.g. linear, non-linear, volume, or curved) profile of the needle tip. For example, if the needle tip is shaped like a linear cone and only half of the needle tip is penetrated into the material based on the needle stroke and penetration depth, the "hole" or indentation made in the material is three and two-dimensionally different than if the needle tip is more, fully/beyond fully inserted into/or, fully penetrates, the material. Thus, needle tip characteristic, shape, volume displacement, stroke, depth, and other characteristics disclosed herein can affect the indentation and penetration made to the material by the needle. When referring to volume displacement a comparison of indention to displacement of water can be used as an illustration. As a volume or imprint is made to a material by a needle, the imprint (displacement of the material by that needle) creates a displacement of material according to this needle-volume insertion. This volume displacement can be computer-characterized with consideration of material deformation properties and material compression properties. As such, computer modeling can consider these material characteristics in modeling indentation deformation properties applied by the needle to the material.

Referring still to FIG. 2, the needle-point pen 200 includes an ink reservoir 230 and pall point ink applicator 235 adjacent to the reciprocating needle 205. The ink application portion (230/235) can include a barrel 240 within which the ink 230 is held. The ball applicator tip 235 can be pressed against a reduced diameter opening of the pen barrel 240 such that a portion of the ball 235 extends therefrom. As the ball 235 is pressed against a material (not shown), the ball 235 is rotated and ink 230 is applied to the material. The needle 205 and ball 235 pen 200 can be repositioned such that the needle 205 is reciprocated over previously applied ink to the material by the ball 235. The indentations and penetrations of the needle 205—point 215 to the material (not shown) can be applied to the material prior to the ink 230 curing/reacting/drying. Thus, the ink 230 may be pressed or inserted into the material by the needle tip 215 immediately subsequent to application of the ink 230 to the material by the ink applicator in the form of a ball-point 235 adjacent pen and ink 230 reservoir.

As shown in FIG. 2, the barrel 210 of the needle 205 can be pressed (or urged) downwards against a material. Similarly and/or separately, the barrel 240 associated with the ball-point 235 ink 230 applicator can be urged (or pressed) downwards against the material. The downwards force of the needle barrel can be different than the downwards force of the ball-point 235 ink 230 applicator. And, a reciprocating force applied to the needle 205 can also be in addition to the downward force applied to the needle barrel 210. Further, a fluidic pressure applied to the ink 230 urging the ink 230 toward the ball 235 can be in addition to the downward force of the ink barrel 240 as shown in FIG. 2.

Ink chemicals and chemical compounds can include pigment bases, and colours that they produce such as:
  Mercury—Red;
  Lead—Yellow, green, white;
  Cadmium—Red, orange, yellow;
  Nickel—Black;
  Zinc—Yellow, white;
  Chromium—Green;
  Cobalt—Blue;
  Aluminum—Green, violet;
  Titanium—White;
  Copper—Blue, green;
  Iron—Brown, red, black;
  Barium—White;
  Ferrocyanide/Ferricyanide—Yellow, red, green, blue; and
  Carbon—Black.

In addition to those listed above, chemicals such as arsenic, calcium, lithium and sulphur are often used, as well as some organic chemical compounds. Lightening agents and materials are sometimes blended with the pigment bases (to reduce production costs). These can include titanium and lead.

A carrier is the ingredient tasked with transferring the pigment. The carrier can be a solvent, with which the pigment is mixed. The carrier runs into the material in the area around where the insertion is made by the needle-point pen. Carriers also serve the function of keeping the mixture of the pigment even and regular, and excluding potentially dangerous pathogens, where applicable. Water can be used as a carrier. Water is not usually as effective as alcohol-based carriers, which may increase an amount of ink which can be absorbed by the material. Examples of alcohols may include methanol, glycerine, rubbing alcohol, denatured alcohol, and propylene glycol.

Other kinds of ink can include glow-in-the-dark ink, link that reacts to UV light, and removable or dissolvable ink.

Another factor can be texture and make-up of the ink. Inks can be light and free-flowing as opposed to thick and viscous. However, with thin inks, colours may not show up as strong, brightly, or intensely.

Traditionally, the viscosity of printing ink has been measured using the efflux cup. This is a container of specified dimensions with an accurately sized and shaped hole at its base. The number of seconds required for the given volume of ink to drain out through the hole gives a measure of its viscosity. A viscometer with an optional integrated thermometer makes it possible to obtain temperature-corrected readings instantly, without having to adjust the temperature of the sample or perform any calculations.

One of the most common instruments for measuring kinematic viscosity is the glass capillary viscometer.

In coating industries, viscosity may be measured with a cup in which the efflux time is measured. There are several sorts of cup—e.g. Zahn cup, Ford viscosity cup—with usage of each type varying mainly according to the industry. The efflux time can also be converted to kinematic viscosities (centistokes, cSt) through the conversion equations. In the printing industry ink viscosity measurement using a viscosity cup and a stopwatch is still considered to be the historical standard against which all other viscosity measurement techniques are referenced. There are numerous viscosity cups available, however, two viscosity cups, EZ Zahn #2 and Din 4, are the most commonly used.

A solid-state viscosity sensor, based on bulk acoustic wave (BAW) technology, uses a piezoelectric sensing element excited by a high-frequency oscillator and operates in the thickness shear mode (TSM) of vibration. In this mode, shear displacement occurs on the crystal faces in the plane of the crystal plate.

Thus, the viscosity of the ink can be varied to a higher, or lower viscosity measured in efflux time in seconds, centistokes, etc. The efflux time in seconds may be between 22 and 28 seconds, and a centistokes viscosity signature #2 can be between 57 and 90, for example. An EZ Zahn #2 (cup-seconds) may vary between 22.5 seconds and 32.5 seconds and vary in 1 second based on a difference between 16 and 22 degrees Centigrade of the ink calibrated sensor measurement vs. temperature for varied (10 percent to 20 percent) concentration of ethanol mixed into Flint CF, for example (white ink translated into EZ Zahn #2 cup-seconds and the associated error).

Thus, the viscosity of the ink can be varied based on a controlled temperature of the ink and/or chemistry of the ink (e.g. % ethanol or % carrier/% pigment). Thickeners and dilatants can also be used to control viscosity and viscosity sensors can be used to sense and measure aqueous and solvent-based viscosity of inks. Thus, an ink can be controlled and varied with intentional or computer-controlled viscosity in 0.1 second, 0.2 second, 0.5 second, 1 second, 2 second or larger increments, for example.

Referring to FIGS. 3A and 3B, a needle-point pen 300 is illustrated. The needle-point pen 300 includes a barrel/shaft 305 and a needle 310. The barrel 305 includes an internal ink reservoir(s) 315 that surrounds the needle 310. FIG. 3A shows the needle 310 in an extended position and FIG. 3B shows the needle 310 in a retracted position. The needle 310 retracts from the extended position of FIG. 3A inwards into the barrel 305 to the retracted position shown in FIG. 3B. While the extent, size and depiction of the Figures depicted herein may be exaggerated, or not drawn entirely to-scale, the teachings illustrated thereby can be appreciated by one of ordinary skill in the art.

Referring again to the comparison of FIGS. 3A and 3B, a "stroke", difference or delta in position 320 between the retracted and extended positions of the needle 310 are illustrated. And, this stroke 320 can defined a retracted state of the needle 310 within the barrel 305 as shown in FIG. 3B and an extended state of the needle 310 beyond the barrel 305 as shown in FIG. 3A. As shown in FIG. 3B, at the retracted state, a tip 325 of the needle (or more of the needle's length) is held within the ink of the reservoir 315 created by the barrel 305. And in the extended state shown in FIG. 3A of the needle 310, the needle 310 extends beyond the ink reservoir 315 to apply ink to a material (not shown) via an indentation or penetration of the needle 310 into the material.

As shown in FIGS. 3A and 3B, the barrel 305 can create the reservoir 315 of ink, dye, liquid, solution, etc. around the needle 310. The barrel 305 and its defined reservoir 315 can include supporting ribs 330. The supporting ribs 330 can provide periodic mechanical supports for the needle 310 during reciprocation/oscillation. And, the supporting ribs 330 may not be entirely circumferential in support around a diameter of the needle 310 such that ink is allowed to flow along the length of the barrel 305 through the supporting ribs 330 to the next portion of the ink reservoir 315. Thus, the ink can be in communication between adjacent chambers of the reservoir 315 defined by the needle-supporting ribs 330 there-between. As such, intermediate mechanical support is supplied to the needle 310 by the ribs 330 of the barrel 305 while allowing the ink/fluid to flow there-between and along the outer surface of the needle 310.

As such, the ink may also be designed to provide a lubricating effect between the needle 310 and supporting ribs 330 during movement of the needle 310. And, the barrel 305 and/or ribs 330 may be made of a low-wear or lower relative hardness as opposed to the needle 310 in order to increase a low-friction reciprocation of the needle 310 there against. For example, the needle 310 may be made of a relatively hard material as opposed to the ribs 330/barrel 305. And, the barrel 305 and ribs 330 may be replaced periodically to replace worn ribs 330 due to friction wear with the needle 310, or vice versa. In some embodiments, the barrel 305 and ribs 330 may be made of a plastic and the needle 310 may be made of a metal. And, material attributes of the barrel 305/ribs 330 may be material self-lubricating with respect to the material of the needle 310.

As shown in FIGS. 3A and 3B, the barrel 305 may include an opening 335 that is sized to correspond to the diameter of the needle 310. As shown in end-profiles of FIGS. 3C and 3D, the opening 335 may be sized to fit around the needle 310, but include ink deposition channels 340 around the diameter of the needle 310 to further allow application of ink to the material in addition to that carried by the needle 310. Again, the ink application channels 340 may be sized for a desired ink application to the material and a property of the ink (such as viscosity or a fluidic pressure of the ink) may also be controlled, or predetermined, for a desired ink application.

Figure 4:
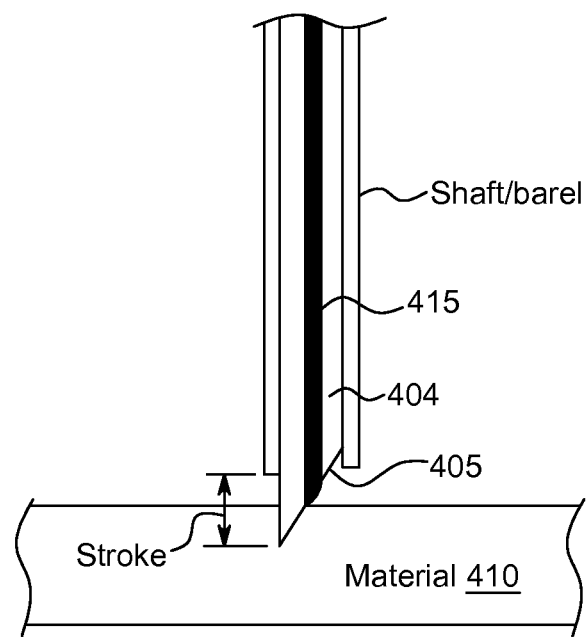

Referring to FIG. 4, the needle can include an internal ink vain. The internal ink vain can extend along an internal length of the needle and provide ink to an application end or tip of the needle. The tip of the needle where the ink vein can be a point of insertion of the tip into a material in an extended position due to reciprocation out of an end of a barrel.

As shown in FIG. 4, the end 405 of a needle 400 can be angled to form a point. The angled end 405 can be relatively sharp at a large angle to the length of the needle 400 or the angle of the tip 405 can be relatively dull at a relatively small, or blunt, angle to the length of the needle 400 shaft. The point of insertion made into a material 410 may be off-center in the angle tip needle 400 as shown and create an indention or penetration into the material 410 according to the shape of the needle tip 405. Ink 415 can be applied to the material 410 by an ink 415 vein (as shown) and the ink 415 vein can be in communication with an ink 415 reservoir (not shown) or the ink 415 vein itself can act as an ink 415 reservoir.

Penetration of the needle 400 into the material 410 can be partial as shown in FIG. 4 where the end 405 of the ink 415 vein is not penetrated into the material 410. Penetration of the needle 400 tip 405 can be increased from that shown in FIG. 4 so as to penetrate the ink 415 vein into the material 410. And, the depth of the needle tip 405 can be controlled; and the depth of the ink 415 vein into the material 410 can likewise be controlled by the reciprocation extent of the needle 400 and/or a reciprocation force applied to the needle 405 urging its end 405 into the material 410.

Moreover, the ink 415 pressure, viscosity, etc. can also be controlled or varied as discussed herein in addition to the needle 400 characteristics/parameters.

Figure 5:
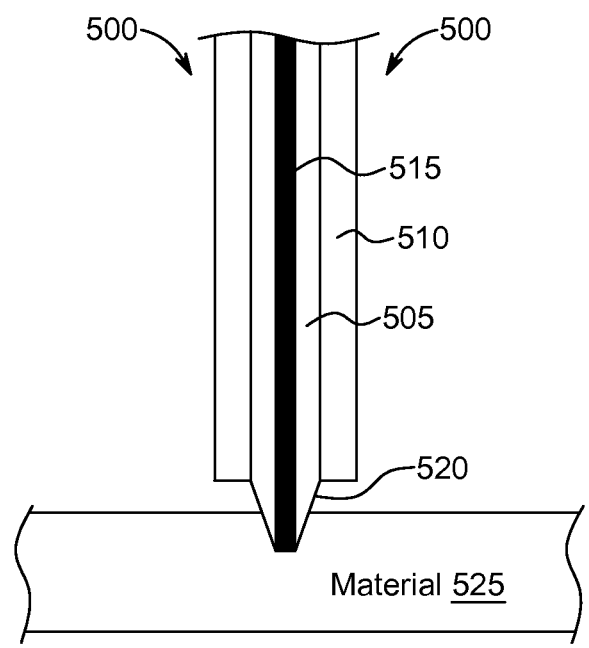

Referring to FIG. 5, center-point needle-point pen 500 is illustrated. As shown, a needle 505 is held and reciprocates within a barrel 510. The needle 505 includes an ink 515 vein within the needle 505. In this embodiment, a tip 520 of the needle 505 is "cone-" shaped with the angled tip 520 having a center-point as shown in FIG. 5. The tip 520 of the needle 505 includes an end of the ink 515 vein that deposits the ink 515 at a center-most point (e.g. a tip 520) of the needle 505, and as a result a deepest point of insertion of the needle 505 tip 520 into a material 525.

As previously discussed, a depth of the needle 505 into the material 525 can be controlled, the frequency of oscillation of the needle 505 can be controlled, and ink 515 characteristics such as viscosity and fluidic pressure can be controlled. The reciprocation position of the needle 505 can be controlled and/or the pressure of the needle 505 against the material 525 can be controlled. The stroke of the needle 505 can be controlled and the rapidness of extension and/or retraction and dampening characteristics of the needle 505 oscillation can be controlled. Thus, any needle 505 characteristic can be controlled as discussed herein and any ink/dye/fluid 515/chemistry can also be controlled as disclosed herein using the needle-point pen 500 shown in FIG. 5.

Figure 6:
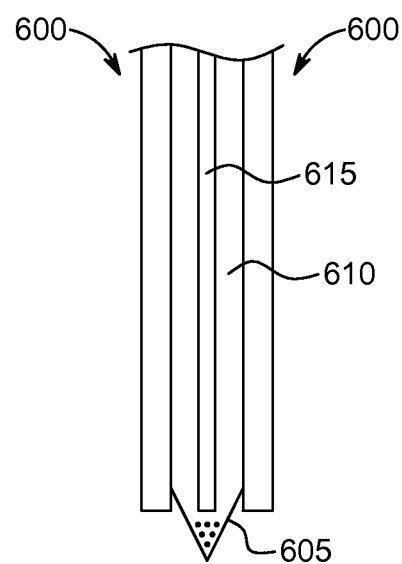

Referring to FIG. 6, a needle-point pen 600 including a porous and/or ink permeable tip 605 is illustrated. As shown, the needle 610 includes an ink vein 615 providing ink to the tip 605 of the needle 610. Disposed at the tip 605 of the needle 610 is the porous and/or ink permeable portion of the tip 605. This porous/permeable portion of the needle tip 605 allows for ink to move from the vein 615 to outside of the tip 605 for application to the material (not shown) when the needle 610 is impacted and/or penetrated and/or pressed into the material.

Porosity or void fraction is a measure of the void (i.e., "empty") spaces in a material, and is a fraction of the volume of voids over the total volume, between 0 and 1, or as a percentage between 0 and 100%. There are many ways to test porosity in a substance or part, such as industrial CT scanning. The term porosity is used in multiple fields including pharmaceutics, ceramics, metallurgy, materials, manufacturing, earth sciences, soil mechanics and engineering.

Porosity can be proportional to hydraulic conductivity; for two similar sandy aquifers, the one with a higher porosity will typically have a higher hydraulic conductivity (more open area for the flow of ink), but there are many complications to this relationship. Porosity of the needle tip 605 can be designed for a viscosity of ink and desired flow therethrough. And, tips 605 of the needle 610 or the needle 610 itself can be changed or replaced as porosity changes (e.g. gets plugged) or to vary the desired flow of fluid (e.g. ink) there through.

Figure 7:
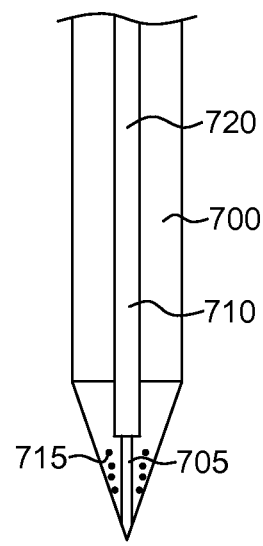

Referring to FIG. 7, a needle 700 can include various smaller veins 705 extending from a main vein 710. The smaller vein(s) 705 can be akin to pores 715 in that they allow ink 720 to flow to a material (not shown) outside of the needle 700 via the veins 710/705 and/or pores 715. The veins 710/705 may be used in connection with the porous 715 material to increase, decrease, and/or control the flow of the ink to particular locations of the needle 700. For example, sides (or tapered sides of a tip) of the needle 700 may receive more ink than an absolute tip of the needle 700.

Figure 8:
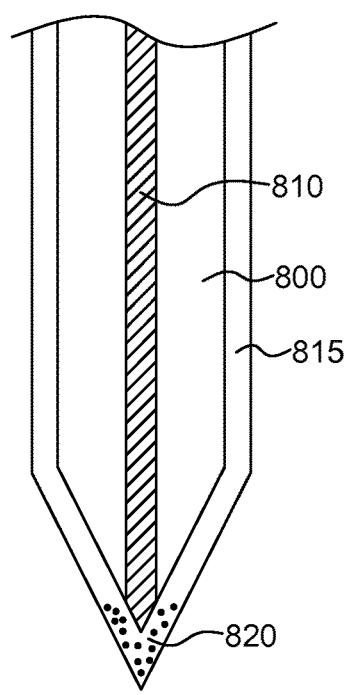

FIG. 8 illustrates a needle 800 with an ink vein 810 and a replaceable tip (or tip "cap") 815. The replaceable tip 815 can wear out and be replaced over the needle 800 itself or be replaced for sterility concerns. The tip 815 may be of a relatively softer or harder material than the needle 800. The material of the tip 815 can be a plastic and the material of the needle 800 can be metallic. The tip 815 can include veins 810 and/or pores 820 that can be in fluidic communication with one or more veins 810 of the needle 810 carrying ink or other fluid.

Figure 9:
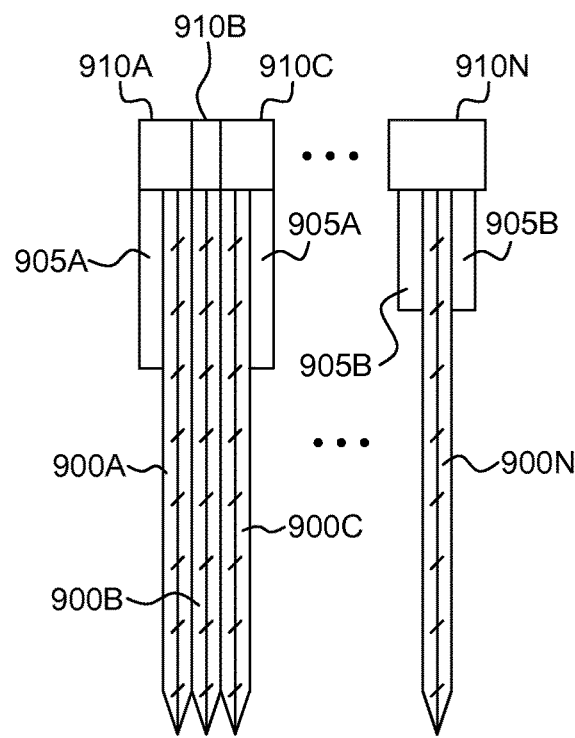

Referring to FIG. 9, there can be a plurality of needles 900A-N held immediately adjacent to one-another. The plurality of needles 900A-N can function as a single needle with multiple tips, or the plurality of needles 900A-N can function independent of one another.

A needle 900N can be associated with a single barrel 905B or a single barrel 905A may support multiple immediately adjacent or spaced needles 900A-C supported thereby. Again, each needle 900 can be associated with its own control device 910A-N or multiple needles 900 can be associated with a common control device 900. Each control device 910 can control each, or multiple, needle characteristics. And, each control device 910 can control ink associated with each, or multiple, ink characteristics.

Figure 10A:
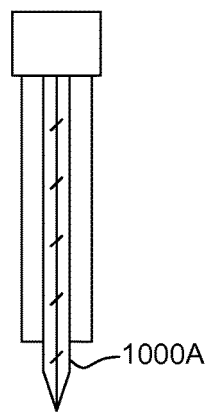
Figure 10B:
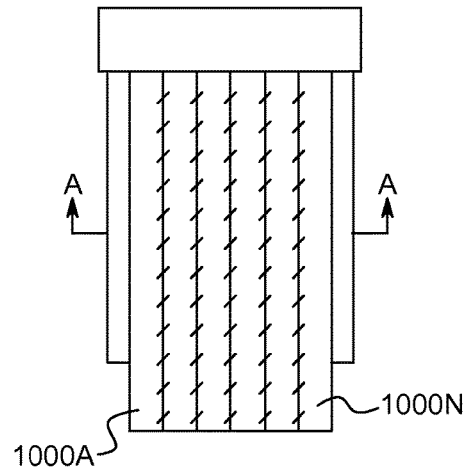

As shown in FIGS. 10A and 10B (FIG. 10A is a cross-sectional perspective of FIG. 10B) needles 1000 may have a triangular cross-sectional tip design from a first perspective (FIG. 10A) with a non-triangular cross-sectional tip design from a perpendicular perspective (FIG. 10B). That is, from the first perspective shown in FIG. 10A the tip of needle 1000A can be triangular shaped, but from the perpendicular perspective of FIG. 10B the tip of the needle 1000A can be flat (or square) and create a flat indentation with relation to adjacent needles 1000A-N. Thus, where the tip of the needle 1000A when viewed from FIG. 10A appears to make a relatively jagged or sharp penetration the relatively flat tip configuration of Needle A in FIG. 10B appears to make a relatively flat and continuous indentation with relation to an adjacent needles. Thus, the indentation characteristics of adjacent needles (or a series of indentations of a single needle) can be designed to create a different indentation property in an X- or Y-direction. Similarly, the depth, colour, needle tip properties, needle actuation and reciprocation properties, and ink properties of adjacent needles and/or a series of indentations and marking made by the same needle can be varied. And, the different depth characters of needles as well as the tip design of needles can create different indentation characteristics in the Z direction. As such, marking control can further include control of adjacent needles and ink characteristics and subsequent or preceding needle pen use.

Thus, indentation and dye characteristics can be varied in the X-, Y-, and/or Z-directions due to needle and ink control as disclosed herein.

Figure 11:
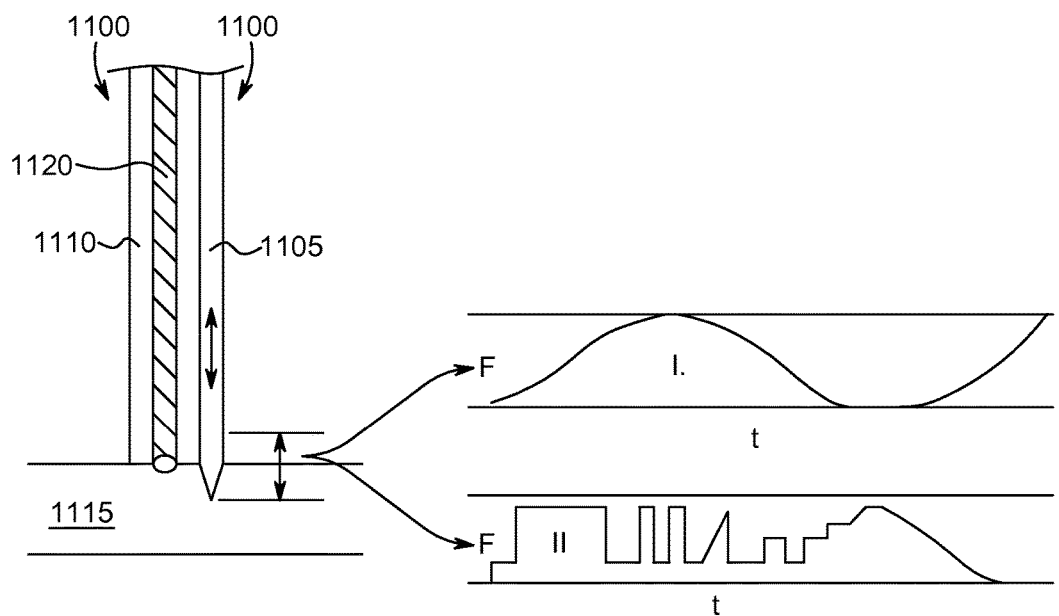
FIGS. 11 and 12 illustrate example of needle and ink control.

Referring to FIG. 11 property profiles I-V are illustrated in connection with a needle-point pen 1100. The property profiles I-V can be related to a needle property and/or an ink property of the needle-point pen 1100. The needle-point pen 1100 can include a needle 1105 and/or ink applicator 1110. As shown, the needle 1105 can reciprocate, or move, in relation to a material 1115. The needle 1105 can be adjacent to the ink applicator 1110 (e.g. a ball-point applicator as shown). The needle 1105 can also include an internal, adjacent, and/or surrounding ink supply and/or reservoir 1120.

The property profiles I-V illustrated can relate to a retracted and extended position of the needle 1105. The property profiles I-V illustrated can relate to a force applied to the needle. The property profiles illustrated can relate to a fluidic pressure. The property profiles shown can relate to a pneumatic pressure if the needle is driven by pressurized air. The property profile shown can relate to hydraulic or mechanical pressure. The property profile shown can relate to a pressure of ink, flow level of ink, or other fluidic property.

As shown by property profile I, the property (vertical axis) can vary over time (horizontal axis) according to a curve. The property can vary over time according to a harmonic oscillation (e.g. according to a sine wave or sinusoid or partial wave. The sine wave, or sinusoid, is a mathematical curve that describes a smooth repetitive oscillation. It is named after the function sine, of which it is the graph. It occurs often in pure and applied mathematics, as well as physics, engineering, signal processing and many other fields. It's most basic form as a function of time (t) is:

$$y(t) = A \sin(2 \pi f t + \varphi) = A \sin(\omega t + \varphi)$$

where:

A=the amplitude, the peak deviation of the function from zero.

f=the ordinary frequency, the number of oscillations (cycles) that occur each second of time.

$\omega = 2\pi f$, the angular frequency, the rate of change of the function argument in units of radians per second \varphi=the phase, specifies (in radians) where in its cycle the oscillation is at t=0.

When \varphi is non-zero, the entire waveform appears to be shifted in time by the amount \varphi/ω seconds. A negative value represents a delay, and a positive value represents an advance.

Property profiles over time can further include square, triangle, and saw tooth waveforms of different properties which may describe a variation of the property in-time.

Figure 12:
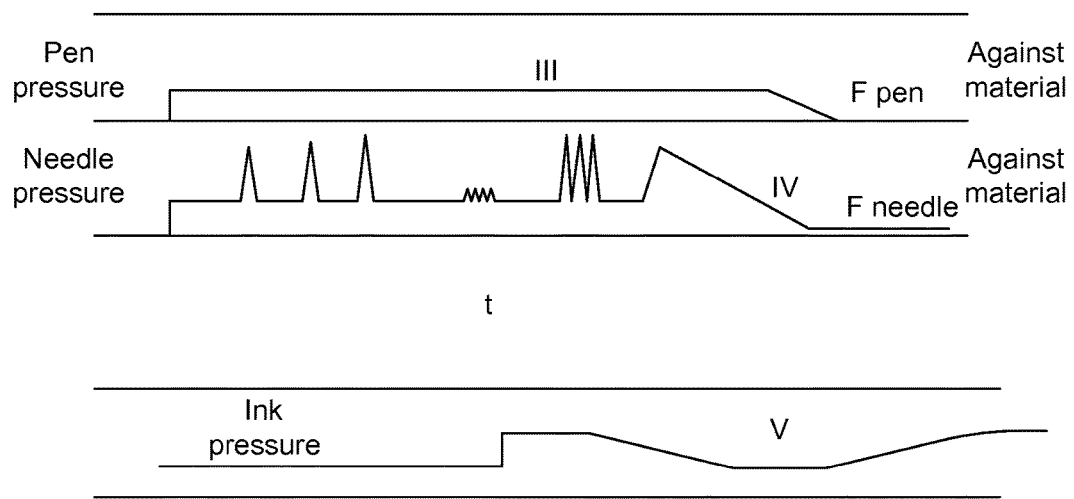

For example, referring to FIG. 12, various examples of property profiles are illustrated for overall pen pressure (III), needle pressure (IV), and ink pressure (V). Various variations of property profiles can be controlled in the marking of material using the needle-point pen as disclosed herein. The needle can reciprocate between 75 hertz and 200 hz in some embodiments. In some embodiments, the reciprocation can be adjusted by a computer or tuner to 1-5 hz increments between 90 and 134 hz, for example.

Figure 13:
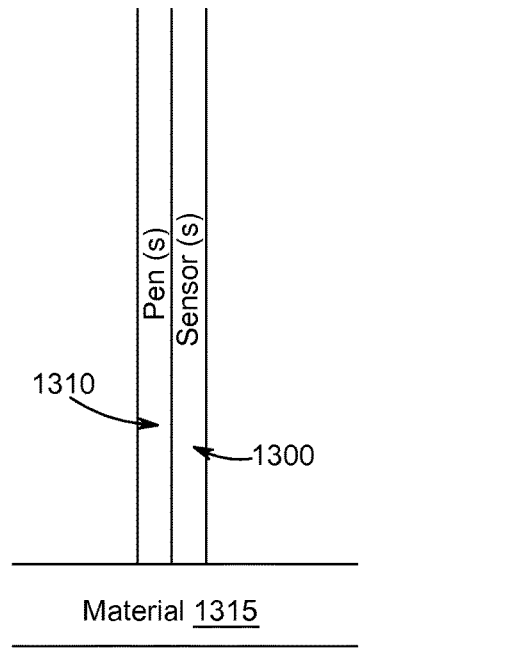
FIGS. 13, 14, 15, and 16 illustrate needle control and movement.

Referring to FIG. 13, other sensor(s) 1300 can be added to control the needle-point pen(s) 1310. For example, a pressure sensor 1300 can sense pressure and material 1315 response to pressure applied thereto. The sensors 1300 may include a material ductility sensor 1300, which can be used to control a property of the needle-point pen 1310. The ductility or other property of the material can be sensed by a reaction of the pen 1310 by the sensor 1300 when the pen 1310 impacts or presses against the material 1315. An optical sensor 1300 can be used to sense optical properties of the material 1315 that may be used to control the needle and/or ink of the needle-point pen 1310. An adhesion or permeability of the material 1315 can also be sensed and the needle and/or ink of the pen 1310 can be controlled based on this sensed property of the material 1315. The sensor 1300 may also consider whether the ink is "running" or "smearing." The sensor 1300 may also consider application of the dye in intensity, colour, amount, or precision by a ink applicator of the pen 1310. The sensor may also measure material 1315 "roughness," "glossy-ness", absorption properties and other material 1315 properties. The optical (or spectral) attributes sensed can measure attributes of the material 1315 (e.g. living tissue viability or blood flow according to a heat sensor or MRI) prior to, and after, application of an indention/penetration by the needle of the pen 1310 and prior to and after application of the dye, ink, or other treatment by the pen 1310.

The sensed attributes may also measure a "curing" or time-related property of the material 1315 or previous or current treatment of the material 1315. For example, where a dye is applied a time-based property of the dying process can be considered for application of a second dye or reapplication of a second treatment of dye to the material 1315. Similarly, an indentation may be made by the pen 1310, the indentation may be sensed, and a subsequent indentation or treatment may be determined based on a property of the material 1315 sensed.

Figure 14:
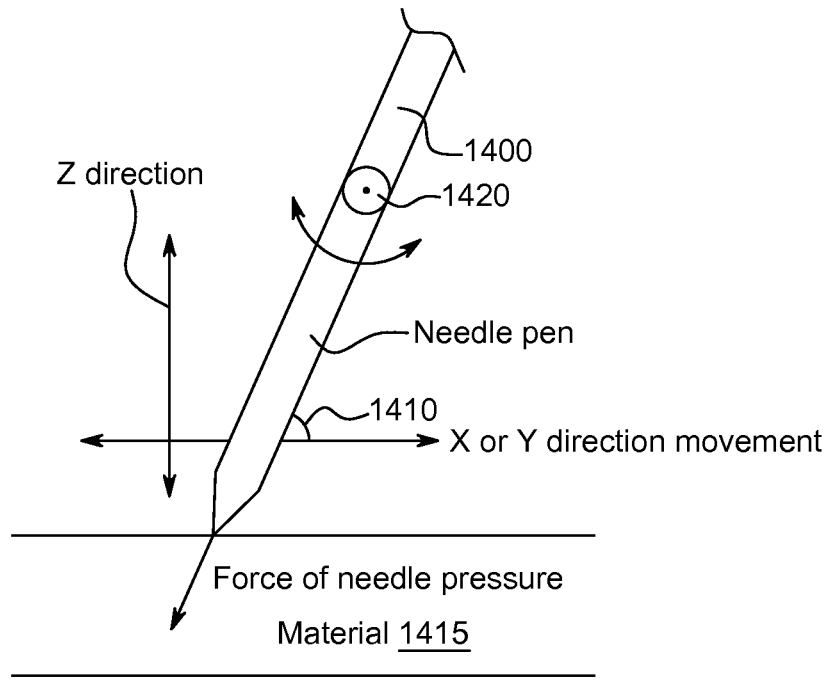

Referring to FIG. 14, an angle 1410 of a needle 1400 may be controlled. The angle 1410 of the needle 1400 may be in regards to an X-, Y-, and/or Z direction (or axis). The angle 1410 of the needle 1400 may also consider a movement of the needle 1400 in the X-, Y-, and/or Z-direction.

For example, in FIG. 14 the needle 1400 is disposed at an angle 1410 to the X- (and/or Y-) direction, as well as the Z-direction. In addition, the needle 1400 may be moved in the X-, Y-, and/or Z-direction(s). For example, referring to FIG. 14 assume that the needle 1400 is angled to the Z-direction and in the left-to-right direction (X- or Y-direction). Then, the needle 1400 is moved to the left, the needle 1400 would be reciprocating as shown into a material 1415 as it is moved to the left. And, when the needle 1400 is moved to the right and is reciprocating at its angle 1410, the needle 1400 would be being dragged away from its penetration into the material 1415.

The angle 1400 of the needle 1400 can fixed in-place. Instead, the needle 1400 can be fixed to a pivot point 1420 to change the angle 1410 of the needle as shown in FIG. 14. The pivot point 1420 can be located at a distance from the tip of the needle. Therefore, the needle 1400 can be rotated to different angles 1410 relative to the X-, Y-, and Z-directions. The needle 1400 can also be rotated, if desired, in particular where the needle 1400 has a different cross-sectional profile as discussed with reference to FIGS. 10A and 10B, for example.

The needle 1400 can also be rotated during reciprocation and/or during contact with the material 1415. Thus, the needle 1400 can be controlled via a "swiping" motion about the pivot point 1420 applying a reciprocating pressure of the needle 1400 against the material 1415.

The needle 1400 can also be translated (e.g. left or right) in the X-, Y-, and Z-direction while rotated about the pivot point 1420 thereby moving the entire needle 1400 while there is a "swiping" motion of rotation of the needle 1400 imparted thereto.

Figure 15:
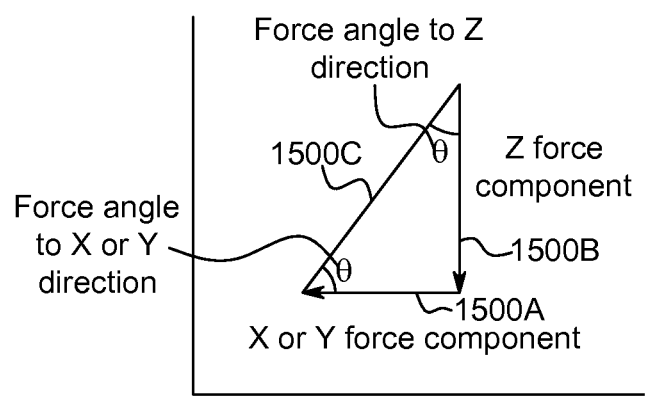

Referring to FIG. 15 different forces may be applied in different directions, or components of different directions to a needle and/or needle-point pen. For example, as shown in FIG. 15 a force 1500C may be applied to a needle, or needle-point pen, that has an X-, and/or, Y-, component 1500A and/or Z component 1500B. Thus, the force 1500B in the downwards Z direction may be different than the force 1500A in the left and/or right X- and/or Y direction. And, combined into a resultant force 1500C of reciprocation in a diagonal force 1500C direction.

Figure 16:
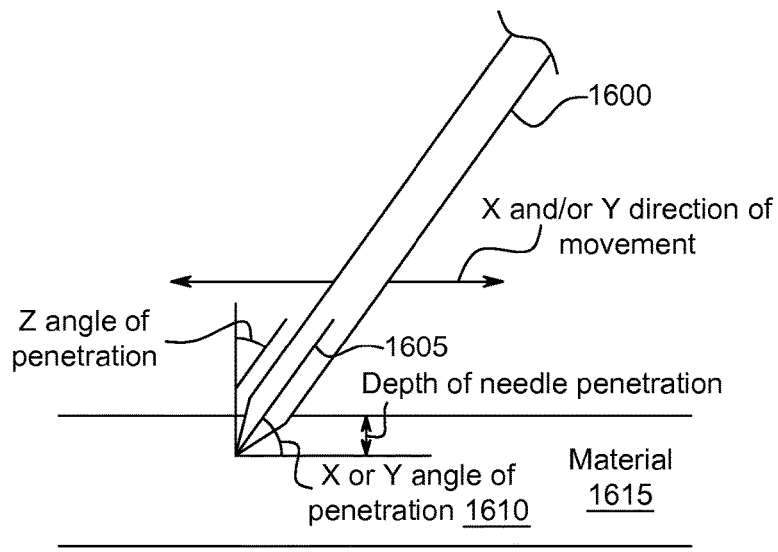

Referring to FIG. 16, the movement of a needle 1600 (e.g. containing an ink vein 1605) can be relative to an angle 1610 of the needle and a depth of penetration of the needle 1600 into a material 1615. Thus, translational control, angle, frequency of reciprocation, extent, force, and ink properties of a needle (1600)-point pen can all be controlled and sensed properties can also be considered in control of material 1615 marking using the needle (1600)-point pen.

Figure 17:
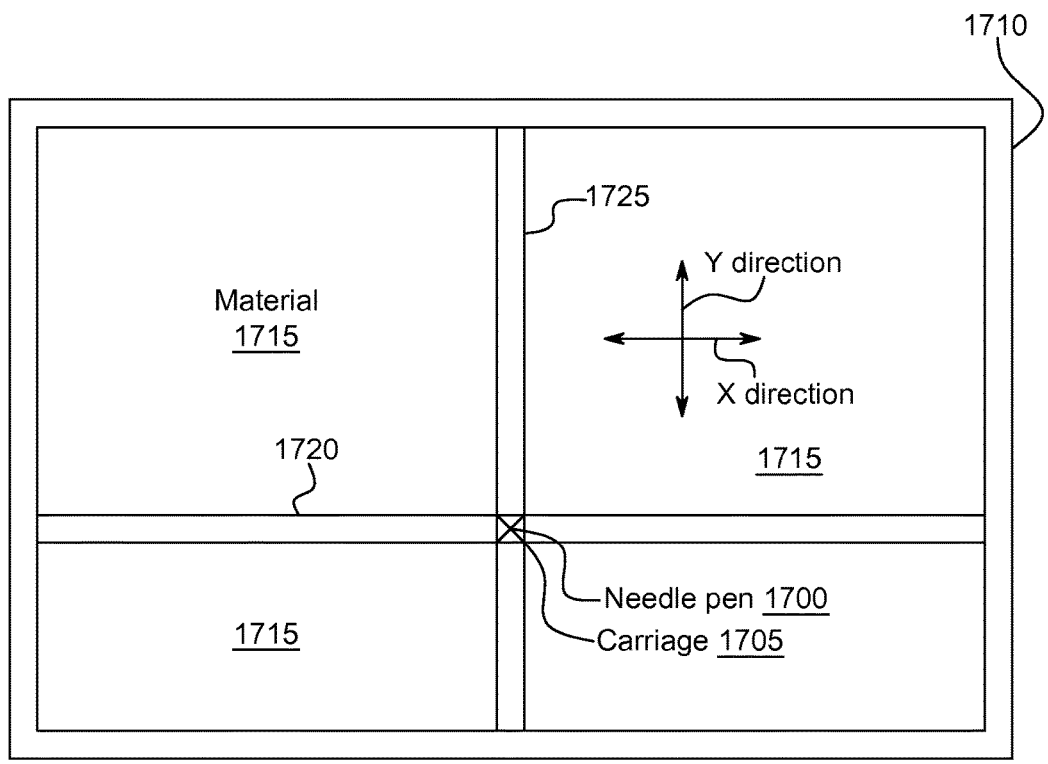
FIGS. 17, 18, and 19 illustrate needle-point pen carriages, movement, and positioning for two and three dimensional marking.

Referring to FIG. 17, the needle-point pen 1700 can be disposed on a carriage 1705. The carriage 1705 can define a location of the needle-point pen 1700. In a two-dimensionally articulated movable carriage 1705 embodiment, the carriage 1705 is moved and positioned in an X- and Y-direction. Thus, the carriage 1705 holding the needle-point pen 1700 is disposed at any location within a X- and Y-space within the capabilities of movement of the carriage on a table 1710.

According to the example shown in FIG. 17, the carriage 1705 can be located in the X-direction at any position along a X-direction track 1720. And, the carriage 1705 can be located in the Y-direction at any position along a Y-direction track 1725. Thus, the carriage 1705, and tip(s) of the needle-point pen(s) 1700 can be located at any two-dimensional location of the material 1715 as shown in FIG. 17. And, the carriage 1705, can be moved to (and held statically held, or moved dynamically over time) any possible location of the material 1715 as shown in FIG. 17.

Figure 18:
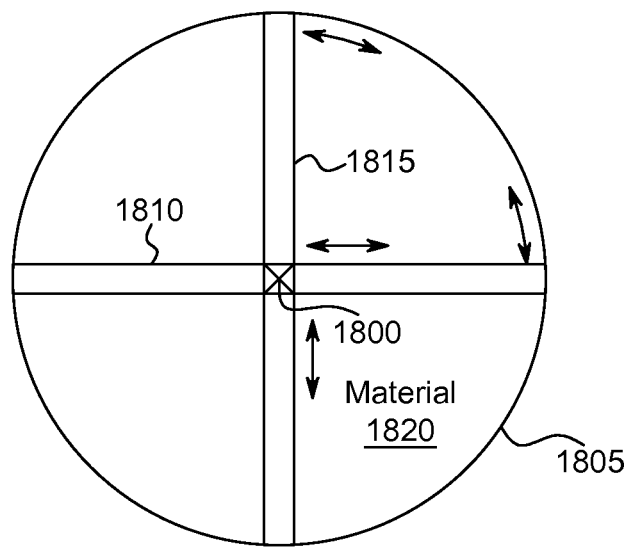

Referring to FIG. 18, a carriage 1800 and table 1805 design is shown where the ends of the tracks 1810 and 1815 in the X- and Y-directions are rotatable about a periphery of the table 1805. Thus, the tracks 1810 and 1815 themselves can be rotated with respect to material 1820 placed on the table 1805 to translate the carriage 1800 in a two-dimensional and angle-specific manner over the material 1820 surface. As such, the angle of the perpendicularly disposed tracks 1810 and 1815 over the material 1820 can likewise be changed to make more complicated translation of the carriage 1800 in directions other than only a Cartesian coordinate system possible according to control of this rotation during simultaneous linear translation of the carriage 1800, for example. Similarly, the material 1715/1820 itself can be rotated or translated in a linear and/or rotational manner with relation to the carriage 1705/1800 and/or tracks 1720/1810 and 1725/1815 in FIGS. 17 and 18 according to some embodiments, such as an incrementally sheet of material feeding/providing system.

Figure 19:
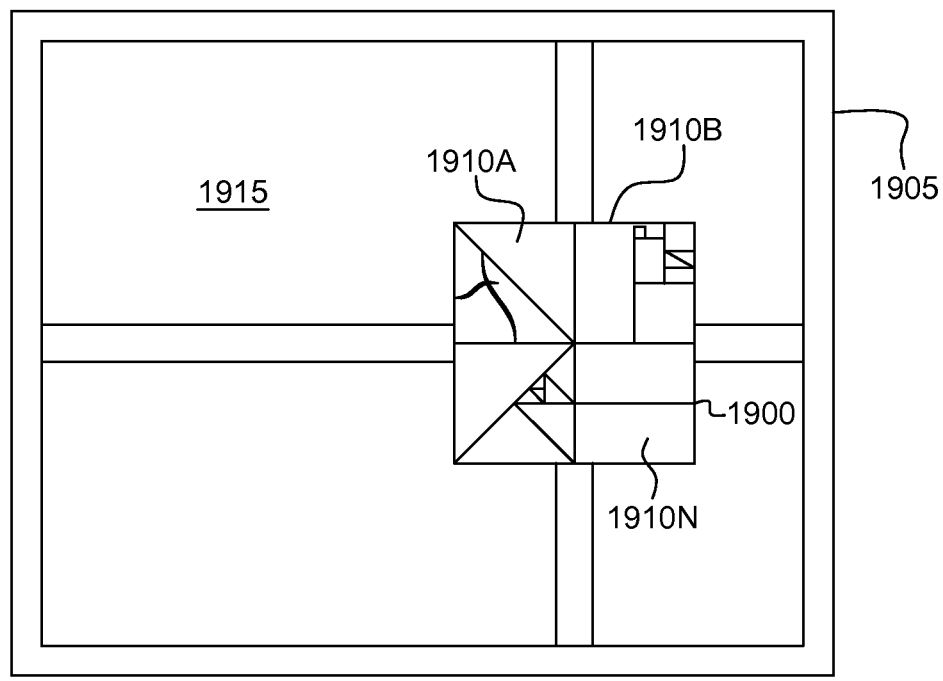

Referring to FIG. 19, a carriage 1900 including an inter-carriage needle-point pen system is illustrated. The carriage 1900 itself can include a coordinate system within the boundaries of the carriage 1900 and the needle-point pen can be moved about within these confines of the carriage 1900 while the carriage 1900 is moving about a table 1905 or is stationary. The carriage 1900 and/or table 1905 can be divided into quadrants 1910A-N and multiple needle-point pens (not shown) can be disposed upon the carriage 1900 and "responsible" for marking the material 1915 within that quadrant 1910. The overall carriage 1900 can be moved to reposition multiple independent marking devices (e.g. needle-point pens) over an area of the material 1915 and the pens can conduct simultaneous and/or sequential marking of the material. The different marking devices can also be applying a treatment at one location of the material 1915 while a needle-point pen is marking the material 1915 with indentations and/or ink at another location of the material 1915 and both devices can be located on the carriage 1900 along with sensors and other control apparatus to coordinate the marking, sensing, and repositioning of each device.

As shown in FIG. 19, the marking, sensing, and repositioning of each device can be divided into one of several quadrants 1910A-N of the carriage 1900. The quadrants 1910A-N of the carriage 1900 can also be associated with a texturing technique or capability of a marking tool. Thus, the quadrants 1910A-N can be divided into square, triangular (e.g. fractal growth), and/or non-linear quadrants 1910A-N. Translation/dynamic movement of a marking device(s) can be controlled linearly in a perpendicular, angled (e.g. triangular/radially polar), and/or curved manner by the carriage 1900.

Various software and computer controlled algorithms including interpolation, line and curve estimation, quad trees, fractals, etc. can be used to control translation, design creation and marking, and property changes during the marking of the material 1915 by the marking utensil, including one or more needle-point pens.

Certain marking techniques have been found using texture and marking techniques with the needle tip pen described herein that are similar in design to those traditionally made with conventional pencils, pens and brushes.

Stippling, for example, is the creation of a pattern simulating varying degrees of solidity or shading by using small dots. Such a pattern may occur in nature and these effects are frequently emulated by artists. Similarly, the needle-point pen can be used to create such artistic effects using varying degrees of solidity or shading by using small dots.

In a drawing or painting, the dots are made of pigment of a single colour, applied with a pen or brush; the denser the dots, the darker the apparent shade—or lighter, if the pigment is lighter than the surface. This is similar to—but distinct from—pointillism, which uses dots of different colours to simulate blended colours.

In printmaking, dots may be carved out of a surface to which ink will be applied, to produce either a greater or lesser density of ink depending on the printing technique. In engraving, the technique was invented by Giulio Campagnola in about 1510. Stippling may also be used in engraving or sculpting an object even when there is no ink or paint involved, either to change the texture of the object, or to produce the appearance of light or dark shading depending on the reflective properties of the surface: for instance, stipple engraving on glass produces areas that appear brighter than the surrounding glass. The needle-point pen can be used to make such dots in printmaking.

The technique became popular as a means of producing shaded line art illustrations for publication, because drawings created this way could be reproduced in simple black ink. The other common method is hatching, which uses lines instead of dots. Stippling has traditionally been favored over hatching in biological and medical illustration, since it is less likely than hatching to interfere visually with the structures being illustrated (the lines used in hatching can be mistaken for actual contours), and also since it allows the artist to vary the density of shading more subtly to depict curved or irregular surfaces.

Images produced by halftoning or dithering and computer printers operate on similar principles (varying the size and/or spacing of dots on paper), but do so via photographic or digital processes rather than manually. These newer techniques have made it possible to convert continuous-tone images into patterns suitable for printing, but artists may still choose stippling for its simplicity and handmade appearance. The Wall Street Journal still features stippled and hatched portraits known as hedcuts in its pages, a holdover from its earlier avoidance of photographs.

In description of flora species, a stippling is a kind of pattern, especially in the case of flowering plants, produced in nature that occur on flower petals and sepals. These are similar to the dot patterns in artworks that produce an often intricate pattern. An example can be seen on the base of the petal insides of *Calochortus luteus*, a poppy endemic to California, for example.

Hatching is an artistic technique used to create tonal or shading effects by drawing (or painting or scribing) closely spaced parallel lines. (It is also used in monochromatic heraldic representations to indicate what the tincture of a "full-colour" emblazon would be.) When lines are placed at an angle to one another, it is called cross-hatching.

Hatching is especially important in essentially linear media, such as drawing, and many forms of printmaking, such as engraving, etching and woodcut. In Western art, hatching originated in the Middle Ages, and developed further into cross-hatching, especially in the old master prints of the fifteenth century. Master ES and Martin Schongauer in engraving and Erhard Reuwich and Michael Wolgemut in woodcut were pioneers of both techniques, and Albrecht Dürer in particular perfected the technique of crosshatching in both media.

Artists use the technique, varying the length, angle, closeness and other qualities of the lines, most commonly in drawing, linear painting and engraving.

The main concept is that the quantity, thickness and spacing of the lines will affect the brightness of the overall image, and emphasize forms creating the illusion of volume. Hatching lines should always follow (i.e. wrap around) the form. By increasing quantity, thickness and closeness, a darker area will result.

An area of shading next to another area which has lines going in another direction is often used to create contrast.

Line work can be used to represent colours, typically by using the same type of hatch to represent particular tones. For example, red might be made up of lightly spaced lines, whereas green could be made of two layers of perpendicular dense lines, resulting in a realistic image.

Thus, the needle-point pen can be used to create certain stipple and hatching techniques, for example, and patterns of marking using the needle-point pen.

For additional examples:

Linear hatching—Hatching in parallel lines. Normally the lines follow the direction of the described plane.

Crosshatching—Layers of hatching applied at different angles to create different textures and darker tones. At its simplest, a layer of linear hatching is laid over another layer at a 90° angle, to which further diagonal layers may be added. Other methods include layering arbitrary intersecting patches. Crosshatching in which layers intersect at slight angles can create a rippled moiré effect.

Contoured hatching—Hatching using curved lines to describe light and form of contours.

Figure 20:
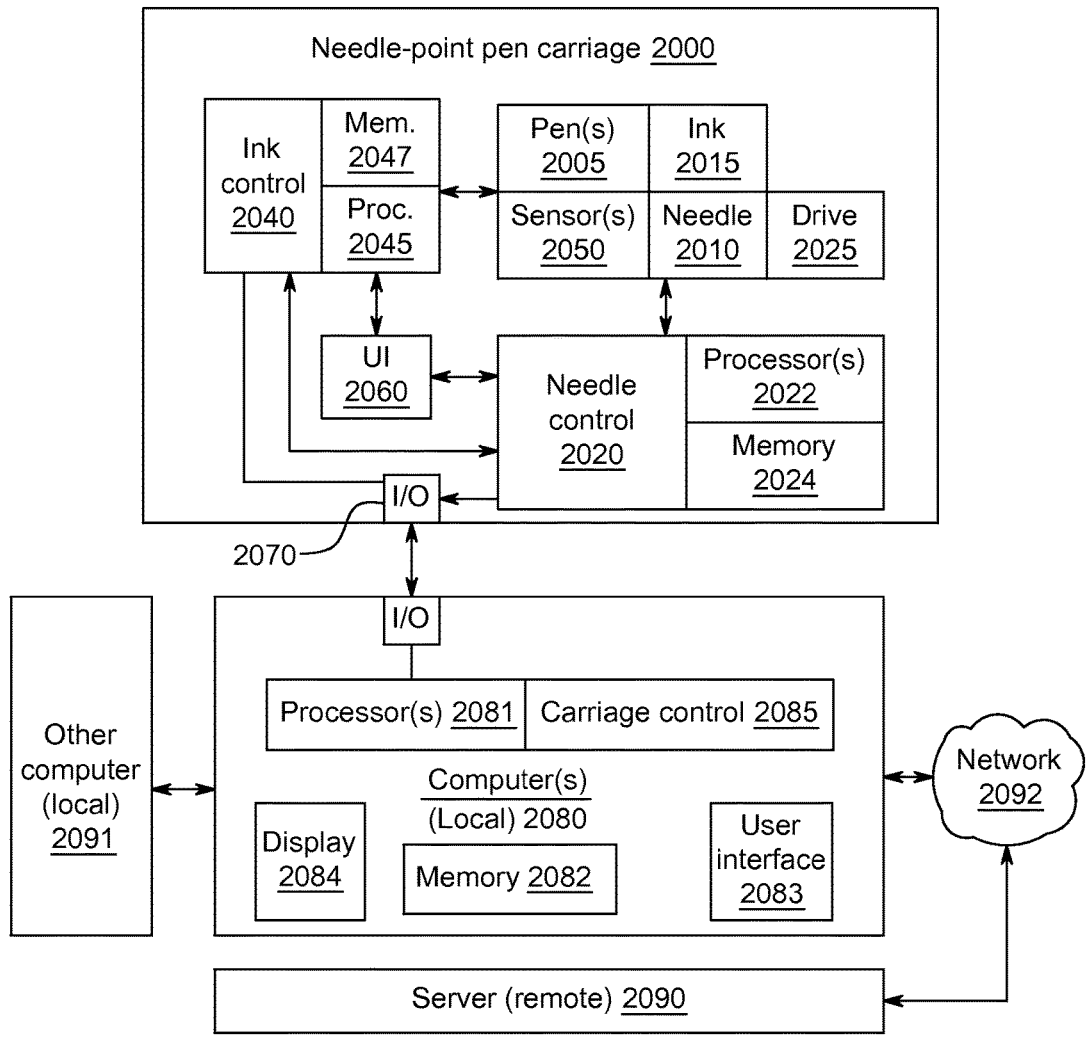
FIG. 20 illustrates components of needle-point pen control, components of a carriage and computer control of the needle, ink, and carriage.

Referring to FIG. 20 components of a carriage 2000 are shown. The carriage 2000 can include one or more needle-point pen(s) 2005. The needle-point pen 2005 can include a needle 2010 and an ink reservoir 2015. The ink reservoir 2015 can include multiple ink reservoirs 2015. The ink reservoir 2015 can include a red ink reservoir, a blue ink reservoir, a yellow ink reservoir, and a black ink reservoir, for example.

The carriage 2000 can include a needle control module 2020 and ink control module 2040. The needle control module 2020 can operate a needle driver 2025. The driver 2025 can oscillate the needle 2010 at a controlled and determined oscillation having oscillation properties as disclosed herein. The driver 2025 can provide a driving force to the needle 2010 and reciprocate the needle 2010 between a retracted position and an extended position as well as positions there between according to an oscillation profile as disclosed herein.

The ink control module 2040 can control ink 2015 properties. The ink control module 2040 can control delivery of ink from the one or more reservoirs 2015 to the needle 2010, a vein within the needle 2010, and/or an ink void surrounding the needle 2010, for example.

The carriage 2000 can include sensors 2050. The sensors 2050 can sense material attributes, such as ductility, colour, curing properties, etc. The sensors 2050 can communicate with the ink control 2040 and needle control 2020 modules. The ink control module 2040 can include a processor 2045 and memory 2047. The memory 2047 can include random access memory (RAM) and/or read only memory (ROM). The processor 2045 can include any logic device including a field programmable gate array and/or a microprocessor. Similarly, the needle control module 2020 can include a processor 2022 and memory 2024. The memory 2024 can include RAM and/or ROM. The processor 2022 of the needle control module 2020 can include any logic device.

The needle control module 2020 can also include the driver 2025 for oscillating/reciprocating the needle 2010. The actuator of the driver 2025 can translate rotational motion into linear motion of the needle. Electro magnets can also be used as well as other transducers as part of the driver 2025. A transducer is a device that converts one form of energy to another. Energy types include (but are not limited to): electrical, mechanical, electromagnetic (including light), chemical, acoustic, and thermal energy. The needle control module 2020 causes a force to be applied to the needle 2010 to change a position, force, rotation, and/or other needle characteristic. An actuator is a transducer that accepts energy and produces the kinetic energy of movement (action)—a driving force. The energy supplied to an actuator might be electrical or mechanical (pneumatic, hydraulic, etc.). An electric motor and a hydraulic cylinder are both actuators, converting electrical energy and fluid power into motion for different purposes. Thus, the needle control module 2020 and/or driver 2025 can include an actuator. A magnetic cartridge, for example, converts relative physical motion to and from electrical signals. Various other position sensors, accelerometers, strain gauges, tactile sensors, rotary and linear motors, and other electro-mechanical devices and sensors can be included to actuate the needle 2010.

The carriage 2000 can include a user interface 2060. The user interface 2060 can provide control feedback to a user as to needle and ink control and status characteristics. The user interface 2060 can also provide trouble-shooting or problem identification to a user such as a worn needle 2010 or a level of ink in the reservoir 2015 in addition to information about the needle 2010, ink 2015, and/or material being worked on.

The user interface 2060 may also track and provide updates as to project completion to the user and/or software and control parameter updates to the control module 2020 and needle module 2040. And, a user may provide control feedback to the control modules 2020 and 2040 of the carriage 2000 using the user interface 2060 or make a break in marking procedure for ink reservoir and/or needle replacement or other adjustments. Similar reservoir and needle replacements as well as adjustments can also be conducted by the carriage 2000 itself where the carriage 2000 has additional "spare" or replacement parts potentially having the same or different ink and/or needle characteristics.

The carriage 2000 can include a communication interface/port 2070. The communication interface 2070 can be wired or wireless. The communication interface can receive and transmit data with a communication interface 2082 of a computer 2080. The computer 2080 can be a computing device that is external to the carriage 2000. The carriage 2000 can also carry a computer thereon or therein with computing processors and may or may not include some or all of the needle and ink control modules 2020 and 2040.

As shown in FIG. 20, the computer 2080 is external to the carriage 2000 in this embodiment. The computer 2080 is communicably connected for communication with the carriage's 2000 needle control module 2020 and ink control module 2040 as well as control of the carriage 2000 position itself. The computer 2080 includes one or more processors 2081 and one or more memory 2082. The memory 2081 stores executable instructions (e.g. stored software and/or hardware) which cause the carriage 2000 to perform certain functions and processes. The computer executable instructions stored on memory 2082 of the computer 2080 and executed by the processor 2081 of the computer 2080 can be in communication and interact with computer executable instructions stored on the memory 2047 and 2024 and executed by the processors 2022 and 2045 of the carriage 2000 to coordinate needle and/or ink control as discussed herein.

The memory 2024 and 2047 of the carriage 2000 and/or memory 2082 of the computer 2080 can further store data in the form of tables, control parameters, and calibration values for needle and ink control. Data stored in tables, stored control parameters and calibration values can also be updated by data received from sensors 2050 disposed on the carriage 2000 regarding needle 2010, ink 2015, and/or material attributes. The data and stored values can be updated as changes to material, marking schemes, programs, designs, layers, digital models, and instructions, as well as needles and ink attributes change.

The computer 2080 can further a carriage position control module 2085 to control the position of the carriage 2000 over material. As previously discussed, the carriage 2000 may be supported and articulated by one or more tracks. The carriage 2000 can also be positionable by one or more articulated arms to which it is attached. Thus, the carriage 2000 can be positionable in two or three X-, Y-, and/or Z-directions. The carriage 2000 can also be oriented and positionable with relation to angles to various axis's and radial positions from center points at a distance as previously discussed. The carriage 2000 can also be moved, or translated in position, at a rate over time and distance dynamically. Thus, the carriage 2000 can be steadily moved, or moved according to a movement scheme to control marking of the material by the needle-point pen.

The carriage 2000 can include multiple needle-point pens, reciprocating needles, ink applicators, and/or sensors. The multiple devices can operate independent of one another and be articulated within the periphery in a coordinated and computer controlled manner according to instructions, software, and algorithms.

The computer 2080 can include one or more user interfaces 2083 such as a keyboard, mouse, touch pad, input stylus, etc. The computer 2080 can also include one or more displays 2084 for providing information to a user. The computer 2080 can include material marking design virtual interface allowing for the user to design a marking scheme using the computer 2080 that is imparted to the material using the needle-point pens 2005 in conjunction with the carriage 2000.

The computer 2080 may be in communication with other computers 2091 designed for certain tasks or in collaboration with the computer 2080 communicably connected to the carriage 2000 and one or more devices (e.g. control modules 2020 and 2040) disposed on the carriage 2000. The computer 2080 may also be in communication with a network 2092 and other remote computer servers 2090. The other computer 2091 and server 2090 may store and provide material models and models and procedure instructions for use by the computer 2080 in commanding the carriage 2000 and tools for manufacturing/marking an article.

Figure 21:
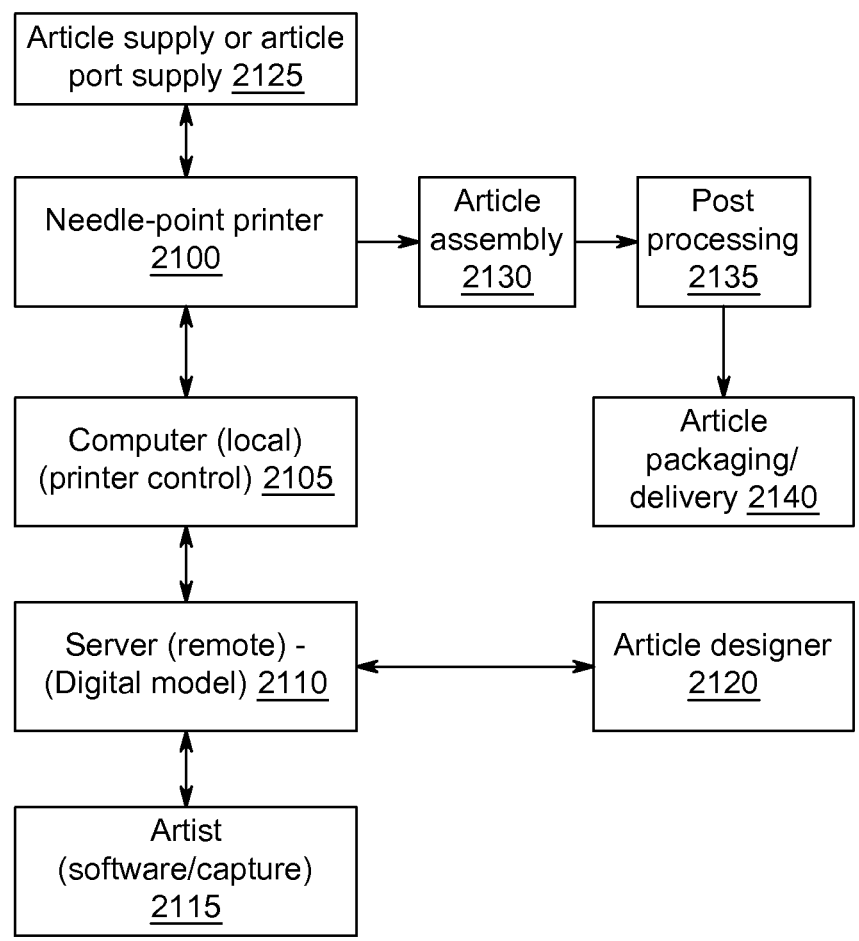
FIG. 21 illustrates a computer implemented process for designing, marking, manufacturing, and providing articles to a purchaser.

Referring to FIG. 21, a process for manufacturing and/or marking an article is illustrated. In some embodiments, the article includes a wearable article such as footwear (e.g. shoes), bags, hats, gloves, jackets, etc. In some embodiments, the article includes a piece of furniture, art, or a decorative article. Thus, in addition to utilitarian marking and manufacturing, the needle-point pen and various inventive devices disclosed herein enable creative artistic tool. And, by harnessing the electronic, chemical, mechanical, fluidic, positional, and other needle, ink, and carriage automated control using actuators, computers, motors, electronics, etc.—new and improved artistic designs may be achieved thereby.

As shown in FIG. 21, a needle-point printer 2100 is provided. The needle-point printer 2100 can include a needle-point pen disposed on a carriage, e.g. as shown in FIGS. 17-20. As shown in FIG. 21, the needle-point printer 2100 can be a two dimensional needle-point printer 2100 where the carriage is positionable in at least two perpendicular directions (e.g. X- and Y-directions). The needle of the pen is reciprocated with an Z-direction component against the material.

The needle-point printer 2100 imparts marks via the needle and dye to the material according to control instructions received from a computer 2105. The computer 2105 is communicably coupled to the needle-point printer 2100 to instruct the needle-point printer 2100 as to marking of the material using a needle-point and dye applicator marking and/or manufacturing design.

The computer 2105 can be considered local to the printer 2100 in that it is in direct communication with the printer 2100 and converts a design received and/or generated into printer recognizable control instructions for the printer 2100 to mark material of an article according to the marking design stored by the computer 2105.

The computer 2105 can receive the marking design from a server computer 2110. The server computer 2110 can be considered remote to the printer 2100 in that the "local" computer 2105 is disposed between the server computer 2105 and the printer 2100. The local computer 2105 receives a marking design from the server computer 2110 and controls the printer 2100 to mark the material using the printer 2100 to impart the design to the material.

The server computer 2110 can create and compile the design to be imparted to the material. The server computer can include software that is configured to combine an artistic design with an article design to create a marked article design. The marking of the article is accomplished using the printer 2100 controlled by the local computer 2105 according to the marked article design provided by the server/remote computer 2110. Of course, the server computer 2110 and the local computer 2105 (as well as any of the computing devices) can be combined or further separated into multiple computing devices; but in this illustration of FIG. 21, the separation thereof is used to illustrate the process work-flow creation of a marked article using computer functional modules commanding and controlling article design, marking, and fabrication for a more understandable purpose and broken-down actions or steps to achieve the desired/requested article.

The server computer 2110 can be in communication with two purposed computers. A first computer 2115 can be referred to as an artist computer and a second computer 2120 can be an article designer computer. The server computer 2110 can receive an artistic design from the artist computer 2115. The server computer can provide this artistic design to the article designer 2120 that applies the design to the article's physical characteristics.

For example, where the article is footwear, the artist 2115 can provide an artistic design to the server 2110 and the article designer 2120 can apply this design to the parts of a shoe. For example, the article designer can apply the artist's design to the tongue, heel, sides, toe, etc. parts of the shoe. And, the article designer 2120 can understand how the parts of the shoe are to be assembled and the design applied thereto will be perceived. For example, a design applied to the parts of a shoe by the article designer 2120 using article designing software may digitally model a design that spans different parts of the shoe when assembled. The sides of the shoe may be stitched to the toe and heel of the shoe and the design may need to span those areas of the different parts of the shoe when assembled.

The artistic design 2115 may also be modified or selectively applied to show the design on the viewable surface of the shoe based on a shape or perspective of the shoe. That is, when viewed from a particular view-point, the shoe and design imparted thereto may appear differently than when viewed from a different view-point. These view-point aspects and understanding of article parts and assembly as well as digital modeling thereof can also be further understood using software and algorithms for fitting an artistic, or other mark, to an article or un-assembled components of the article. An example of an automated system and process for manufacturing of shoe parts is known to Nike and other shoe manufacturers such as that discussed in WO 2013/074940, for example, the contents of which are hereby incorporated by reference herein.

Where the printing is to be conducted on an assembled article, a three-dimensional model of the article can be obtained as opposed to more two-dimensional "flat" pieces of the article. The article can be registered such that different portions of the article are understood according to the digital model of the article. The article or parts of the article can be scanned or otherwise sensed to create the model.

Regarding digital modeling of article parts or an assembled three dimensional article, a laser LIDAR scanner can create a point cloud model of the article, or parts of the article, for more accurately modeling the article in three dimensional space. Lidar (also written LIDAR, LiDAR or LADAR) is a remote sensing technology that measures distance by illuminating a target with a laser and analyzing the reflected light. Lidar is popularly used as a technology to make high-resolution maps, with applications in geomatics, archaeology, geography, geology, geomorphology, seismology, forestry, remote sensing, atmospheric physics, airborne laser swath mapping, laser altimetry, and contour mapping.

There are several major components to a lidar system:

Laser—600-1000 nm lasers are most common for non-scientific applications.

Scanner and optics—How fast images can be developed is also affected by the speed at which they are scanned.

Photodetector and receiver electronics—Two main photodetector technologies are used in lidars: solid state photodetectors, such as silicon avalanche photodiodes, or photomultipliers.

Position systems—Lidar sensors that are mounted on mobile platforms to determine the absolute position and orientation of the sensor.

Stereoscopy can also be used to understanding and create three dimensional models of an article for application of a design or other marking. Stereoscopy (also called stereoscopics) is a technique for creating or enhancing the illusion of depth in an image by means of stereopsis for binocular vision. Any stereoscopic image is called a stereogram. Most stereoscopic methods present two offset images separately to the left and right eye of the viewer. These two-dimensional images are then combined to give the perception of 3D depth.

Thus, a three-dimensional model of an article can be sensed, measured, or determined and the design or markings can be applied to the actual article's parts pre-assembly or as a three-dimensional fully assembled article. As such, the design and markings can be considered a "layer" applied to the outer surface of the article using the needle-point pen disposed on a positionable carriage, or articulated arm, for example. And, the article designer can use specialized software and a computer interface to virtually apply the layer design to the outer of surface of the article model, which is subsequently tangibly applied to the actual tangible article by the computer controlled and automated needle-point pen of the printer 2100.

The article designer 2120, or other application specialist, can further use computer assisted packages and computer-based image manipulation and morphing/skewing technology to further enhance, improve of experiment with creative designs and artwork. Such resizing, skewing, stretching, filters, optical enhancements, etc. can be made to create optical effects are improve application of the size, shape, theme, or other features of a design to the article.

Thus, the artist 2115 may use certain tools to create a design which the article designer 2120 can take and use virtual and computer software and manipulation tools to further enhance or change the design applied to the article and visually displayed thereon. As such, the artist 2115 and the article designer 2120 can reach a new and collaborative work together in creation of a design to be applied to the article pre, or post, assembly of the article.

According to some embodiments, the artist 2115 may be a purchaser of the article who makes a design to be applied to the article. In some embodiments, the artist 2115 may design a tattoo that the artist is considering to apply to their own skin. The purchaser of the article may also work with a tattoo artist 2115 in designing the tattoo, but want to see what the tattoo might look like when applied first to a material, such as leather. As such, the artist 2115 can include the purchaser and/or a tattoo artist. The tattoo artist 2115 may also want to develop their skill in creating their art in the form of a design made to leather using the needle-point pen printer 2100. The tattoo artist 2115 may also work with the article designer 2120 or may learn to practice the craft of article design in connection with the tattoo artist's experience in applying tattoos to live skin. The application of various tattoo techniques may also be experimented with by the tattoo artist 2115 using the needle-point pen and computer control to further perfect the tattoo artist craft and new experimental techniques without experimenting on live tissue of a living person where a permanent tattoo is not easily removed (as opposed to disposal of a "tattooed" article. Thus, the markings and designs applied to an article by the needle-point pen printer 2100 may be considered, or coined, "the tattoo that you can take off" by simply removing your shoes, belt, hat, jacket, bag, throwing away a cushion, etc.

The use of the computer control techniques may further enable new marking techniques. The new marking techniques may be somewhat based or inspired by traditional painting, chiseling, engraving, dying, and/or drawing techniques. And, software, image enhancement, warping or other image conversion and software techniques can be used. Further, where the needle-point pen includes a depth characteristic or layers of dye or layers of secondary indentations and penetrations, layers of markings can be used to further enhance possibilities of design creation.

For example, a stippling computer controlled technique or software for control of the needle-point pen can be used. Stippling is the creation of a pattern simulating varying degrees of solidity or shading by using small dots. Such a pattern may occur in nature and these effects are frequently emulated by artists.

In stippling drawing or painting, the dots are made of pigment of a single colour, applied with a pen or brush; the denser the dots, the darker the apparent shade—or lighter, if the pigment is lighter than the surface. This is similar to—but distinct from—pointillism, which uses dots of different colours to simulate blended colours.

Similar techniques can be used or made by computer control of needle and ink characteristics of the needle-point pen of printer 2100 as well as oscillation control, depth control and positional control by the computers 2105, 2115, and 2120.

In printmaking, dots may be carved out of a surface to which ink will be applied, to produce either a greater or lesser density of ink depending on the printing technique. In engraving, the technique was invented by Giulio Campagnola in about 1510. Stippling may also be used in engraving or sculpting an object even when there is no ink or paint involved, either to change the texture of the object, or to produce the appearance of light or dark shading depending on the reflective properties of the surface: for instance, stipple engraving on glass produces areas that appear brighter than the surrounding glass.

The technique became popular as a means of producing shaded line art illustrations for publication, because drawings created this way could be reproduced in simple black ink. The other common method is hatching, which uses lines instead of dots. Stippling has traditionally been favored over hatching in biological and medical illustration, since it is less likely than hatching to interfere visually with the structures being illustrated (the lines used in hatching can be mistaken for actual contours), and also since it allows the artist to vary the density of shading more subtly to depict curved or irregular surfaces.

Images produced by halftoning or dithering and computer printers operate on similar principles (varying the size and/or spacing of dots on paper), but do so via photographic or digital processes rather than manually. These newer techniques have made it possible to convert continuous-tone images into patterns suitable for printing, but artists may still choose stippling for its simplicity and handmade appearance. The Wall Street Journal still features stippled and hatched portraits known as hedcuts in its pages, a holdover from its earlier avoidance of photographs.

The term stipple can also apply to a random pattern of small depressions applied to a surface to increase the friction and make the surface easier to grip. This process is similar to knurling or checkering, but is often used on complex curved surfaces, such as anatomical grips, where a regular pattern would not fit. Stippling can be cast into plastic objects, or applied with a hammer and punch to wood or metal objects.

Stippling may also refer to the circular pattern of dots created around a gunshot wound when a firearm is discharged in very close proximity to the skin.

In quilt making, the term refers to background quilting in heirloom quilts and all-over stitching in others. It is made freehand or with free-motion machine quilting by densely stitching through all layers in a relatively close repetitive design.

In interior decoration, the tips of the bristles of a stippling brush are dabbed onto a freshly painted wall or surface to create a subtle design in the paint. The paint hit by the points is displaced and leaves only a thin dot of paint through which a lighter layer of colour underneath will show through.

In digital photography, stippling refers to image noise similar to film grain.

Thus, stippling techniques that may be enhanced using software and computer control to impart such techniques to articles using the needle-point pen can be used and experimented with.

As another example of using one or more techniques in software or other needle-point pen control can include hatching techniques. Hatching is an artistic technique used to create tonal or shading effects by drawing (or painting or scribing) closely spaced parallel lines. (It is also used in monochromatic heraldic representations to indicate what the tincture of a "full-colour" emblazon would be.) When lines are placed at an angle to one another, it is called crosshatching.

Hatching is especially important in essentially linear media, such as drawing, and many forms of printmaking, such as engraving, etching and woodcut. Artists use the technique, varying the length, angle, closeness and other qualities of the lines, most commonly in drawing, linear painting and engraving.

The main concept is that the quantity, thickness and spacing of the lines will affect the brightness of the overall image, and emphasize forms creating the illusion of volume. Hatching lines should always follow (i.e. wrap around) the form. By increasing quantity, thickness and closeness, a darker area will result.

An area of shading next to another area which has lines going in another direction is often used to create contrast.

Line work can be used to represent colours, typically by using the same type of hatch to represent particular tones. For example, red might be made up of lightly spaced lines, whereas green could be made of two layers of perpendicular dense lines, resulting in a realistic image.

Linear hatching—Hatching in parallel lines. Normally the lines follow the direction of the described plane.

Crosshatching—Layers of hatching applied at different angles to create different textures and darker tones. At its simplest, a layer of linear hatching is laid over another layer at a 90° angle, to which further diagonal layers may be added. Other methods include layering arbitrary intersecting patches. Crosshatching in which layers intersect at slight angles can create a rippled moiré effect.

Contoured hatching—Hatching using curved lines to describe light and form of contours.

Thus, stippling, hatching, and other techniques can be used in software or enhanced in software, or used as an inspiration to create new and exciting marking designs applied to an article using the needle-point pen.

It should be noted, however, that use of the needle-point-pen can be in conjunction with other marking apparatus such as painting, staining, stamping, drawings, etc. which may be manual or automatically carried out.

Referring again to FIG. 21, a new business model (e.g. including a non-profit and/or scholarship model) can be understood. For example, the artist 2115 can be a person (e.g. a student) in a remote country. The artist 2115 may be knowledgeable about a cultural type of art or artistic tool for creating art. Thus, the artist 2115 at the remote location can create art and make this art available for a purchaser to apply to an article of which they select. The article designer 2120 can then apply the artist's design to the article and the article can be shipped or otherwise provided to the purchaser. The artist 2115, for example in a remote location (e.g. in Vietnam, Africa, South America, etc.) may then be compensated for their artistic contribution to the design and manufacture of the article.

According to this model, the remote artist 2115 may impart their culturally-inspired artistic talent to an article's design. And, the article designer 2120 may work with this artist 2115 to create the decorated article according to this artist's 2115 creative work.

The remote artist 2115 may also include a remotely located or inspired article design. For example, where an artist is Dutch and creates a design for a wooden shoe or clog, the artistic design can be imparted to the model of a traditional wooden shoe by the Dutch artist 2115 or someone with Dutch wood shoe design and layout or digital modeling thereof. This design can be imparted to a wood shoe "blank" by the computer controlled needle-point pen of the printer 2100 on-location or remote to the location of the artist 2115. Similarly, the design imparted to the wooden shoe by-hand by the artist 2115 may be image-captured and replicated by the remotely located needle-point printer 2115 based on an image capture, edge detection, colour detection, and/or three dimensional point cloud model that may also include depth characteristics of the wooden shoe design and manual feature creation using traditional tools and methods.

Thus, a purchaser may be given an option to create their own design, or submit their own art for article marking and creation. However, the purchaser may purchase a work or collaboration with a remote artist specializing in creation of related art. For example, a student in Africa creates African-culture (or tribal) "themed" artwork. The charity presents a depiction of this artwork to a purchaser, among other works of art made in different remote locations by different students in those various locations. The purchaser may be allowed to purchase the remote artist's design to be place on a manufactured article of the purchaser's choice. Or, the purchaser may be offer the services of collaboration with the remote artist in a custom-made design. Where the artist has made a particular design with a particular article in-mind, the purchaser may be offered that article with the applied design as a product for purchase.

In this example, the artist submits the design, the purchaser selects the design along with the desired article to which it is applied. The design and article are merged into a final decorated, or marked, article model which is forwarded to the needle-point printer 2100. The needle-point printer 2100 is supplied with the article parts 2125 for printing thereto according to the artist created and purchaser selected design. Or, an already assembled article may be supplied 2125 to the needle-point printer 2100 which applies the design to the article as disclosed herein.

If unassembled, the marked parts of the designed article is forwarded for assembly (if in parts) 2130, post processing (e.g. cleaning, sealing, etc.) 2135, packaged and shipped 2140 to the purchaser. Other aspects of article design, such as size, colour, material, etc. can be taken into account as would be normally considered in order fulfillment and article manufacture.

Then, or at some point, the artist 2115 can be compensated for their contribution to the design by the purchaser. The compensation can be a straight monetary compensation. Or, in the case of a charitable or non-profit component, the monetary compensation can be in the form of a scholarship contribution to the artist 2115 or artist's school, for example in the artist's name for them to use for scholastic endeavors.

The artist 2115 may also be provided with article design and virtual artistic tools to learn new computer-assisted methods for art creation using their personally learned artistic crafts based on local and cultural techniques. And, such techniques can further translate into new and exciting texturing and computer assisted techniques, such as those previously discussed related to stippling and hatching examples.

Further, the materials and media to which art is applied can further take into consideration that which is locally used to do so. For example, where an etching or chiseling procedure is applied to pottery in a locality, potentially with a ceramic/pottery dye, such techniques can also be translated into the creation of computer assisted techniques in connection with use of the needle-point pen and embodiments disclosed herein. Similar techniques can be applied to marking wood, metal, and chemical/dying treatments applied thereto. For example, where a metal is indented using the needle-point pen, a reactant can also be applied in place of, or as part of the dye. The reactant can cause metal to oxidize in a location and upon spectrally sensed oxidation of the metal by the reactant of the dye, a dilatant or neutralizer may then be applied to the metal to cease reaction or discontinue curing of a reactant. Similarly, a dye may be removed or prevented from further curing or spreading. And, after a dye is cured, a portion of the dyed material can be removed by the needle-point pen or a second layer of dye or reactant can be applied thereto to create a second layer of creative design.

Thus, in addition to the needle and ink/reactant control, material control and creative layering of processes can be used to create new, useful, and aesthetic designs applied/printed to articles. And, computer and software visualization and processes can also be translated to the tangible medium using the embodiment disclosed herein.

Figure 22:
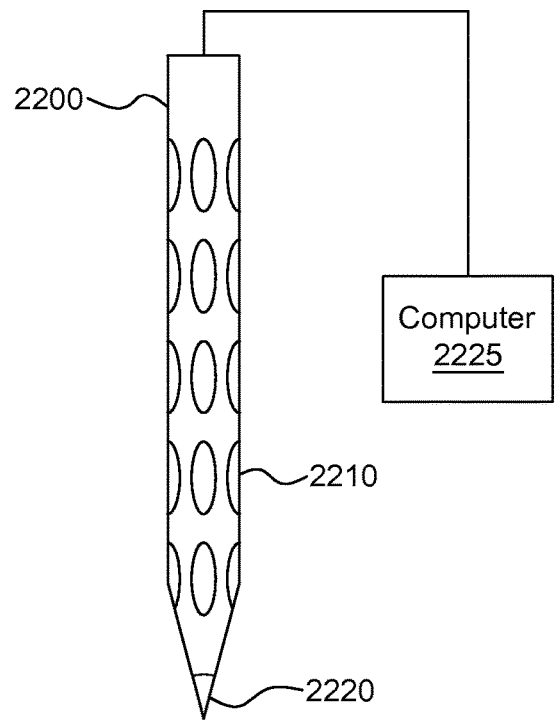
FIG. 22 illustrates a stylus marking technique computer learning sensor/tool.

Referring to FIG. 22, a "learning stylus" 2200 is illustrated for providing computer input as to how an artist controls a marking instrument when marking a material. For example, the stylus 2200 may represent a paint brush, pencil, tattoo machine, engraver, chisel, etc. The stylus 2200 may include various sensors 2210. The sensors can be pressure sensors 2210 disposed about the periphery of the stylus 2200. Accelerometers, tilt sensors, vibration sensors, and other sensors can also be disposed in the stylus 2200. The stylus 2200 may also include pressure sensors located at the tip 2220 of the stylus in addition to around the periphery of the stylus 2210.

As the artist uses the stylus 2200 to practice the artist's craft in a manner typical of the marking tool of which the stylus 220 is meant to represent, the sensors 2210 track and translate the motions and pressure controls to machine learned and learnable techniques for control of the needle-tip pen and even virtual simulation of manual marking tool (stylus simulated) control.

Thus, the learning stylus 2200 of FIG. 22 can also represent a characterization tool to further understand the manner in which an artist uses a conventional marking tool. In addition, certain techniques used by a "master" artist may not entirely be understood by the artist her/himself. And, using computer 2225 recognition and reproduction of movement, new and exciting techniques may be recognized and expanded or replicated using machine control.

For example, a tattoo artist may use a different technique to apply a tattoo to live skin based on a thickness of the skin (e.g. thicker due to body fat content or exposure to sun), texture of the skin (e.g. relatively rough or smooth skin), a colour of the skin, etc. The tattoo artist may also understand from experience tattooing the effects of tattoo "healing" or scarring of the skin and ink depth-related aspects of placing ink within, transdermally, or superficially. These material attributes of marking live skin may translate (or not) to other materials and techniques that may be considered, recognized, and/or otherwise sensed using the learning stylus 2200 in connection with computer 2225 collection of data and analysis thereof. These learned techniques can be characterized with machine control of a needle-point pen, for example. And, such machine/computer learning can further enhance marking techniques used in other areas and with other materials, tools, and mediums.

To reiterate some aspects of the embodiments disclosed herein that relate to the needle-point pen control and use:

There can be mechanical control of the needle. This needle control can include stroke, distance of stroke, pressure, oscillation frequency, impact/velocity/linear and non-linear movement. The needle control related to oscillation can include wave forms, amplitude, frequencies, periods, dependence on force/pressure against the material. The oscillation characteristics can be changed based on pressure or material sensed attributes. The oscillation can be affected by depth of the needle insertion into the material and needle-point characteristics.

The angle of the needle can be changed with regard to the X-, Y-, and Z-axes. The angle can include a rotation of the needle or a swiping motion of the needle which can also affect depth and pressure against the material.

The movement (e.g. translation and position) of the needle and carriage can be changed and controlled in the X-, Y-, and/or Z-direction. The needle-tip pen can be moved into the direction of angled reciprocation or dragged away from this angle of reciprocation and advancement of the needle into the material. The needle can be moved sideways to this angle of reciprocation.

The needle design can be changed in length, support, bending, diameter, thickness, sharpness, bluntness, etc. The material of the needle can be selected based on the material it will impact or be inserted into and can take into account wear characteristics of the needle and an associate barrel support. The needle shape can be selected for indention, taper, cross-sectional shape, etc. A needle design can be selected for sterility, replicability, material ductility and other properties, reaction etc. The needle can have ink/fluid veins, be porous, or otherwise include features, grooves, or other channels for ink supply to the material.

The ink can have controlled or selected characteristics. The ink can have selected spectral, colour, intensity, human viewable or non-viewable (e.g. ultra-violet), fluorescent, characteristics. The ink can have a selected viscosity, adhesive, dispersion, reactive, curing, etching, and acidic, cleaning, or other property. The ink can be an aqueous solution. The ink can be a solvent. The ink can have particles suspended therein. The purpose of the particles can be reactive, texturing, lubricating, colour imparting, etc. The ink can be designed to have a layered effect in conjunction with other layers of ink. The ink may have a reactive "two-part" combination such as an epoxy or fiber-glass resin reactant.

The ink control can include ink pressure, flow, and volume, consider vein diameter and have viscosity that effects pressure, flow, volume, etc. The rate of ink deposition can be considered and depth of indentation as well as indention depth effecting surface area by such indentation or penetration as it relates to a corresponding surface area coverage and desired application of ink thereto.

Other aspects of needle control, ink control, carriage control, and marking creation are discussed herein and explained regarding to various examples and designs as well as the articles created thereby.

Figure 23:
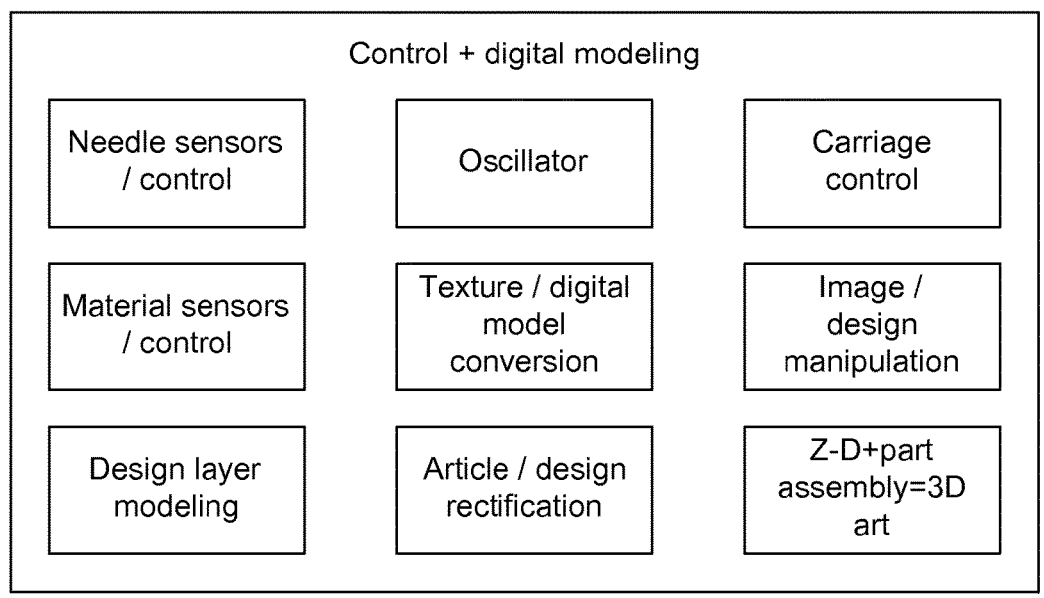
FIG. 23 illustrates functional modules associated with needle/ink control and article digital modeling and design components.

Other examples of software and/or hardware based modules are illustrated in FIG. 23.

Methods, computer systems, computer-storage media, and graphical user interfaces are provided for controlling a needle-point pen, designing articles, applying designs to article design, creating new articles and article assembly and manufacture methods.

Embodiments of the present invention relate to systems, methods, computer storage media, and interactive graphical user interfaces (GUIs) for, among other things, displaying and interacting with performance data for a machine-learned model.

Accordingly, in one embodiment, the present invention is directed to one or more computer-readable media having computer-executable instructions embodied thereon that, when executed by a computing device, cause the computing device to generate a graphical user interface (GUI) for visualizing the design and manufacture of an article using, at least in part a marking tool such as the needle-point pen disclosed herien. The GUI comprises an item representation display area that displays a plurality of item representations corresponding to a plurality of items processed by the machine-learned model.

In another embodiment, the present invention is directed to one or more computer-readable media having computer-executable instructions embodied thereon that, when executed by a computing device (e.g. a server computer, carriage computer, needle-point printer computer, artist computer, article design and/or assembly computer, etc.), cause the computing device to perform a methods, visualizations and manipulations of digital models and manufacturing and marking control procedures as disclosed herein. Additionally, the method includes displaying each of the training item representations corresponding to the each of the plurality of training items and displaying each of the test item representations corresponding to the each of the plurality of test items on a graphical user interface (GUI) to train the artist or article designer to use the software to design the article and/or control the needle-point printer.

An example of an operating environment in which embodiments of the present invention may be implemented is described below in order to provide a general context for various aspects of the present invention. An exemplary operating environment for implementing embodiments of the present invention is a computing device. The computing device is but one example of a suitable computing environment and is not intended to suggest any limitation as to the scope of use or functionality of embodiments of the invention. Neither should the computing device be interpreted as having any dependency or requirement relating to any one or combination of components illustrated.

Embodiments of the invention may be described in the general context of computer code or machine-usable instructions, including computer-usable or computer-executable instructions such as program modules, being executed by a computer or other machine, such as a personal data assistant, a smart phone, a tablet PC, or other handheld device. Generally, program modules including routines, programs, objects, components, data structures, and the like, refer to code that performs particular tasks or implements particular abstract data types. Embodiments of the invention may be practiced in a variety of system configurations, including hand-held devices, consumer electronics, general-purpose computers, more specialty computing devices, etc. Embodiments of the invention may also be practiced in distributed computing environments where tasks are performed by remote-processing devices that are linked through a communications network. In a distributed computing environment, program modules may be located in both local and remote computer storage media including memory storage devices.

The computing device can include a bus that directly or indirectly couples the following devices: a memory, one or more processors, one or more presentation components, one or more input/output (I/O) ports, one or more I/O components, and a power supply. The bus represents what may be one or more busses (such as an address bus, data bus, or combination thereof). One may consider a presentation component, such as a display device, to be an I/O component. Also, processors have memory. Distinction is not made between such categories as "workstation," "server," "laptop," "hand-held device," etc., as all are contemplated within the scope of a "computing device."

An example of a computing device typically includes a variety of computer-readable media. Computer-readable media may be any available media that is accessible by the computing device and includes both volatile and nonvolatile media, and removable and non-removable media. Computer-readable media comprises computer storage media and communication media; computer storage media excludes signals per se. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device. Communication media, on the other hand, embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The memory includes computer-storage media in the form of any combination of volatile and nonvolatile memory. The memory may be removable, non-removable, or a combination thereof. Exemplary hardware devices include solid-state memory, hard drives, optical-disc drives, and the like. The computing device includes one or more processors that read data from various entities such as the memory or the I/O components. The presentation component(s) present data indications to a user or other device. Exemplary presentation components include a display device, speaker, printing component, vibrating component, and the like.

The I/O ports allow the computing device to be logically coupled to other devices including the I/O components, some of which may be built in. Illustrative components include a microphone, joystick, game pad, satellite dish, scanner, printer, wireless device, and the like. Interaction with the I/O components may be via voice, touch, gestures, keyboard, a pointing device such as a mouse, and the like.

Furthermore, although the term "server" is often used herein, it will be recognized that this term may also encompass a search service, a search extender service, a Web browser, a cloud server, a set of one or more processes distributed on one or more computers, one or more stand-alone storage devices, a set of one or more other computing or storage devices, a combination of one or more of the above, and the like.

A data store stored on a computer readable medium of a computing device is described. The data store includes control parameters disclosed herein. For example, the computer executable instructions stored on the memory can include control instructions for controlling the needle, ink, carriage, etc. The stored control parameters can include needle control parameters, oscillation control parameters, ink control parameters, carriage control parameters, material ductility measurements or stored parameters, optically sensed parameters, ink reservoir and colour control parameters, material control parameters, texture sensing and surface sensing parameters, an article design model, a mark application layer model, image enhancement parameters, resizing parameters, shape-fitting, design versions, display considerations, rotation models, effects, and other design characteristics of an artistic rendition. Thus, when stored as a data structure on a computer readable medium, RAM, and/or ROM the medium structure may be moved, accessed, instruction followed, written, rewritten, copied in its tangible form as a non-transitory replication of magnetic, optical, and other media, etc.

Some of the methods and apparatus disclosed herein include needle-based printing with simultaneous or near-simultaneous application of a dye, ink, treatment, or other fluid or solution along with needle penetration. The methods and apparatus can further include other additional independent acts of stamping, cutting, etching, and dying—sometimes simultaneously with needle-based indelible printing.

Many embodiments disclosed herein include computer-aided control of needle and ink parameters as well as two and/or three dimensional movement of an electro-mechanically repositionable carriage supporting one or more reciprocating needles and one or more ink/fluid reservoirs.

A liquid-penetration property of leather can also understood or determined to control a pressure at which a needle inserts ink into the leather. The pressure can be needle pressure and/or independent ink pressure. Based on a pressure of the needle against the leather, a depth of the penetration of the needle into the leather can also be controlled or varied. Other materials than leather can be used such as clay, wood, metal, plastic, fake leather (e.g. "pleather"), ceramic, foam, etc.

A material property of the material (e.g. wood or leather) can also controlled or be varied by applying a liquid or treatment to the material to decrease a resistance to penetration property of the material. The variation of a mechanical property of the material can be modified in a two-dimensional direction. For example, a liquid (or amount of liquid) can be applied to a first location of the material to reduce the material's resistance to penetration by the needle at that location. A duration under which the material is allow to "soak" under application of the liquid can also vary to the material's resistance to penetration. And the application of the liquid to different locations of the material can be different and selected at the different locations of the material with different "soak-times." Thus, a material property including resistance to penetration or puncture resistance can be two-dimensionally varied across a length and width of a material by application of a different amount(s) or time-variable (e.g. "soak" time) at different locations of the material.

The liquid applied to the material can include water. The liquid applied to the material can also include a petroleum-derived liquid or solution. The liquid applied to the material can include a solvent. The liquid can include a dissolvent for breaking down a compound of the material for subsequent penetration by the needle and insertion of the ink/dye/solution into the material. The dye may also be a combination of these liquids with a dye to further disperse the fluid/dye/pigment within the material at the depth of penetration or according to other needle and ink (e.g. fluid and/or solution) control.

Prior to impact of the reciprocating needle with the material (e.g. leather or wood), a ductility of the material can be sensed. The ductility of the material can be sensed by a pressure sensor making physical contact at a location of the material. The ductility, or resistance to penetration, property of the material can be used to determine a pressure applied to the fluid applying needle. As previously discussed, the depth of the insertion of the ink in the material can also be controlled based on both the resistance to pressure or ductility of the material sensed and the pressure applied to the needle during application of the ink at least partially penetrating the material. A surface coat of fluid may also be applied prior to and/or simultaneous with indentation by the needle.

In addition, the control of the depth of penetration of the needle, an angle at which the needle is pressed/reciprocated against the material can also be controlled and varied across two perpendicular directions. For example the needle can be reciprocated at a polar angle to an X-horizontal direction (e.g. left direction) and/or a polar angle to a horizontal Y-direction (e.g. right direction) relative to the perpendicular Z-direction (e.g. vertical or up/down direction) about a point and radius from which the polar angle is measured. And, this angle with respect to the X, Y, and Z directions of pressure and reciprocation of the needle against the material can be varied, controlled in-time, and selectable in amplitude, velocity, impact characteristic (where force applied goes to infinity or results in material (e.g. plastic) deformation) over the surface of the material.

A number of needles impacting the material (e.g. wood, clay, ceramic or leather) and at least partially penetrating the material can also be selected over the two dimensional penetration of the material by the one or more needles, or a different type, width, sharpness, or shape of needle (or needle control method) may also be selected and used as discussed herein.

Moreover an amount of ink supplied to the needle (and/or material simultaneously with impact) can be selected and controlled based on the type of needle or material. In addition, a property of the ink(s) itself can be controlled or made for the type of material. Where a material is relatively hard or resistant to insertion, a dye solution can be used that includes a compound to chemically break-down the material in addition to application of the dye/colourant. The compound can also be designed to control a dispersion of the ink within the material or react to the material to create a varied or different appearance. A bio-reactive agent may also be included in the ink to react with bio-materials particular to bio-based materials such as leather and wood.

Thus, a method of needle-based printing to leather can include a reciprocating needle having an ink delivery system supplying ink to the penetrating needle during reciprocal impact with the leather.

Moreover, according to some embodiments disclosed herein, the dye/fluid can be, or include, a medication which is delivered to a patient via the controlled application and reciprocation of the needle-point pen and fluidic flow and pressure/control as discussed herein. As disclosed, the medication may be "spread" about trans-, sub-, and/or intra-dermal application or a combination thereof (including skin, muscle, tissue/material characteristics, depth, etc. considerations) using the needle-point pen. And, a controlled-release of the application of medicine (e.g. fluid or reactant or medicine release/dissolve/disperse attribute) or dispersive ink/medication property can be controlled based on the depth to which it is injected/penetrated by the reciprocating needle and ink control properties into living (or dying) tissue. Moreover, the needle and/or medication/fluid delivery can be controlled in volume and characteristic extent to appropriately administer the fluid to the patient.

The ink and/or needle control can also consider an induced "scarring" or depth attribute caused to live tissue. For example, where a scar tissue releases medication slower (or faster) in-time, a scaring attribute can be introduced to a living tissue upon needle and/or fluid control. Thus, the tissue/material parameters can be intentionally modified based on an intentionally induced scarring technique. Similar techniques can be applied to marking of "living" wood and/or other bio-living materials as discussed hereinafter in addition to dead wood, leather, ceramic, etc.

Similarly, bio-acceptable creation of living tissue can be created (or urged to be created) by the dye/fluid introduced into a living body according to the embodiments disclosed herein. The introduction of bio-compatible or living tissue promoting growth components can be introduced, or specially introduced in a distributed manner) according to needle and ink/fluid/medication control as discussed herein.

Thus, the fluid can be distributed in two—or three dimensional space to control release to the tissue or other material. Similarly, the tissue and/or other material can be modified by fluidic and/or needle control (e.g. due to scarring and/or location adjacent to previous penetrations and/or blood conduit (e.g., artery and/or vein locality and blood flow direction—e.g. to, or away from, the heart, organ, and/or tumor) or introduce solutions or particle impregnated suspensions there-into.

In addition to "injection" or depth-selective indention mechanical properties and depth-dependent marking, the ink injected/applied/dispersed can have a depth-sensible presence. For example, a sensible marker can be introduced into the ink. The sensible marker can be related to wavelength, magnetism, and/or radio activity. A sensor can be "tuned" to one or more depths and the existence of the propagating dye (for whatever reason) can be sensed at a selected depth.

For example, regarding magnetism, a depth of magnetism can be sensed by a depth-calibrated magnetic sensing head. Similarly, a radio-active depth or material "density" can be sensed via sonar. A liquidity can be sensed, and a permeability to electro-magnetic waves can be sensed.

Thus, according to some embodiments, the dispersion of dye within a material can be sensed and digitally characterized/modeled by injection thereto into the material. And, this dispersion and/or propagated location and/or dilution can be sensed by magnetic, optic, radioactive, sound, density, wave propagation, or other means. For example, a magnetic head may be tuned to a material depth. Similarly, sonar and radioactivity depth can be sensed to density and intensity as well as change (time increase or decrease) as to properties. Optical pick-up can be tuned to frequency as in the case of "Blue-ray" dual-layer data reading and writing. Thus, understanding of compound propagation within a material (e.g. organic, inorganic, living, dead, dying, etc. materials) can be sensed and used to control further (in-time, volume, pressure, extent, movement, location, and/or other needle control and/or . . . ) application of the dye/needle control and/or sensing control and collaboration between all of the parameters disclosed herein.

For example, where a depth fluidic character can be sensed post-application by a needle-point pen, this fluidic characteristic can be used to control subsequent needle and/or dye delivery characteristics including any of the needle and/or dye control parameters disclosed herein. Sensor location and feedback can also be considered.

Deposition of a magnetic or magnetizable material can also be applied by the needle-point pen. For example, a hard disk drive (HDD), hard disk, hard drive or fixed disk is a data storage device used for storing and retrieving digital information using one or more rigid ("hard") rapidly rotating disks (platters) coated with magnetic material. The platters are paired with magnetic heads arranged on a moving actuator arm, which read and write data to the platter surfaces. Data is accessed in a random-access manner, meaning that individual blocks of data can be stored or retrieved in any order rather than sequentially. HDDs retain stored data even when powered off.

Using the needle-point pen, magnetic material (e.g. magnetic ink or suspension of magnetic material) can be deposited on a surface, within an indention, and/or at a particular depth in a material. Data can be read and written to the magnetic material similar to the platter of a hard drive. This magnetic stored data can be saved even when there is no power supplied to the magnetic material.

Further, different data can be stored at differently deposited depths of magnetic material and the head that reads and writes to the magnetic material can be "tuned" to read and write to the magnetic material deposited at different depths. Moreover intermittent layers of material can be laid over a magnetic material deposited material and then another layer of magnetic material may be layer over that material at a relative "depth" that is above the first layer of "printed" magnetic material. The needle of the needle-point pen can also be controlled to deposit the magnetic material within the material such that the magnetic material is deposited at a particular depth within the material and the magnetic material can be read or written to by a magnetically tuned head similar to the magnetic head of a hard drive.

Other needle characteristics can be controlled as to thickness of the needle when depositing magnetic material on, or in, or in at a desired depth of, a material. For example, multiple heads of different widths, depths, etc. can be used as disclosed herein. Use of thinner width needles can increase the data density of magnetic material deposited and increase discrete amounts of data held thereby.

Conductive ink, and printed circuitry can also be deposited within a material using the needle-point pen at different depths within the material. And, multiple layers of material may be overlaid and further printed upon or within using the needle-point pen and inks of various suspensions and chemistry whether magnetic, conductive, capacitive, reactive, etc.

Moreover, sensors may be printed on or within the material. Examples of sensors that can be printed include magnetic sensors, strain gauges (resistors that change with deformation), potentiometers, meters, electrostatic sensors, etc. which can be disposed within the material using the needle-point pen. And, manufacture of printed structures can be even more available and accurate using the computer and electro-mechanical positioning and manufacturing processes discussed herein. Other uses and benefits of the needle-point pen are discussed hereinafter.

As another ink example, a contrast agent fluid can be used by the needle-point pen for internal sensing applications. MRI contrast agents, for example, are a group of contrast media used to improve the visibility of internal body structures in magnetic resonance imaging (MRI). The most commonly used compounds for contrast enhancement are gadolinium-based. Such MRI contrast agents shorten the relaxation times of atoms within body tissues following oral or intravenous administration. In MRI scanners, sections of the body are exposed to a very strong magnetic field causing primarily the hydrogen nuclei ("spins") of water in tissues to be polarized in the direction of the magnetic field. An intense radiofrequency pulse is applied that tips the magnetization generated by the hydrogen nuclei in the direction of the receiver coil where the spin polarization can be detected. Random molecular rotational oscillations matching the resonance frequency of the nuclear spins provide the "relaxation" mechanisms that bring the net magnetization back to its equilibrium position in alignment with the applied magnetic field. The magnitude of the spin polarization detected by the receiver is used to form the MR image but decays with a characteristic time constant known as the T1 relaxation time. Water protons in different tissues have different T1 values, which is one of the main sources of contrast in MR images. A contrast agent usually shortens, but in some instances increases, the value of T1 of nearby water protons thereby altering the contrast in the image. Thus, a contrast agent can be imbedded, injected, or otherwise disposed in tissue of an animal using the needle-point pen.

Similarly, RFID material deposited using the needle-point pen. Radio-frequency identification (RFID) is the wireless use of electromagnetic fields to transfer data, for the purposes of automatically identifying and tracking tags attached to objects. The tags contain electronically stored information. Some tags are powered by electromagnetic induction from magnetic fields produced near the reader. Some types collect energy from the interrogating radio waves and act as a passive transponder. Other types have a local power source such as a battery and may operate at hundreds of meters from the reader. Unlike a barcode, the tag does not necessarily need to be within line of sight of the reader and may be embedded in the tracked object. RFID is one method for Automatic Identification and Data Capture (AIDC).

RFID tags are used in many industries. For example, an RFID tag attached to an automobile during production can be used to track its progress through the assembly line; RFID-tagged pharmaceuticals can be tracked through warehouses; and implanting RFID microchips in livestock and pets allows positive identification of animals. RFID tags can be attached to cash, clothing, and possessions, or implanted in animals and people and imbedded and/or printed on such objects and beings using the needle-point pen.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

What is claimed is:

1. A method of administering a medication using a needle-point pen apparatus, the method comprising:
providing the needle-point pen apparatus, the needle-point pen apparatus comprising:
a barrel;
a needle movably disposed within an inner channel of the barrel, the needle having a tip and an elongate shaft;
a drive coupled to the needle and providing a driving actuation to the needle according to a drive signal, the driving actuation causing the needle to reciprocate within the barrel between one or more extended and retracted positions according to a change in frequency and a change in amplitude of the drive signal, the change in frequency of the drive signal being proportional to an oscillation frequency of the needle by the drive and the change in amplitude of the drive signal being proportional to a force applied to the needle by the drive;
the needle being designed to at least partially insert the medication into living tissue;
a medication reservoir supplying the medication to the needle for at least partial insertion into the tissue; and
a computing device controlling the needle actuation and the supply of the medication to the needle for controlling administration of the medication at multiple different computer-controlled depths and/or locations of the tissue.

2. The method according to claim 1, the computing device further controlling the needle actuation and the supply of the medication to the needle for controlling administration of the medication at the multiple different computer-controlled depths of the tissue.

3. The method according to claim 1, the computing device including:
a processor; and
a memory,
the method further comprising:
the processor accessing needle control parameters stored on the memory; and
the processor executing instructions stored by the memory causing the processor to control the actuation of the needle.

4. The method according to claim 3, the method further comprising the needle control parameters specifying different oscillation frequencies for the actuation of the needle based on different types of needles used by the needle-point pen apparatus.

5. The method according to claim 3, the method further comprising, the needle control parameters specifying different oscillation frequencies for the actuation of the needle based on different tissue attributes to which the medication is administered by the needle-point pen apparatus.

6. The method according to claim 3, the needle control parameters defining multiple different angles at which the needle reciprocates relative to a surface of the tissue and the multiple different angles are not-perpendicular to the surface of the tissue.

7. The method according to claim 1, the method further comprising the needle introducing intentional scarring to the tissue at different locations of the tissue.

8. The method according to claim 1, the needle-point pen apparatus further comprising a carriage supporting at least the barrel, the needle, and the drive, the carriage including at least two dimensional articulating means for positioning the carriage at multiple locations in at least two different angles.

9. The method according to claim 1, the medication including a sensible marker, the sensible marker being sensible when injected into the tissue by the needle.

10. The method according to claim 9, the method further comprising the needle injecting the sensible marker at different depths for selected sensing of the sensible marker at the different depths.

11. The method according to claim 9, the method further comprising the needle injecting the sensible marker at different densities at different depths.

12. The method according to claim 9, wherein the sensible marker includes a contrast agent for magnetic resonance imaging.

13. The method according to claim 1, wherein the medication reservoir is at least partially disposed within the barrel and entirely surrounds the tip of the needle in a retracted position.

14. The method according to claim 1, wherein the needle includes an internal vein providing the medication to the tip of the needle.

15. The method according to claim 1, wherein the tip of the needle includes a porous portion.

16. The method according to claim 1, wherein the tip of the needle includes a medication permeable portion.

17. The method according to claim 1, wherein the needle includes a replaceable tip disposed over the tip of the needle.

18. A method of administering a medication using a needle-point pen apparatus, the method comprising:
providing the needle-point pen apparatus, the needle-point pen apparatus comprising:
a barrel;
a needle movably disposed within an inner channel of the barrel, the needle having a tip and an elongate shaft;
a drive coupled to the needle and providing a driving actuation to the needle, the driving actuation causing the needle to reciprocate within the barrel between one or more extended and retracted positions;
the needle being designed to at least partially insert the medication into living tissue;
a medication reservoir supplying the medication to the needle for at least partial insertion into the tissue; and
a computing device controlling the needle actuation and/or the supply of the medication to the needle for controlling a scarring attribute applied to the tissue to control blood flow to, or away from, a tumor.

19. A needle-point pen apparatus for administering a medication to tissue, the needle-point pen apparatus comprising:
a barrel;
a needle movably disposed within an inner channel of the barrel, the needle having a tip and an elongate shaft;
a drive coupled to the needle and providing a driving actuation to the needle, the driving actuation causing the needle to reciprocate within the barrel between one or more extended and retracted positions;
the needle being designed to at least partially insert the medication into the tissue;
a medication reservoir supplying the medication to the needle for at least partial insertion into the tissue; and
a computing device including computer executable instructions for controlling the needle actuation and supply pressure of the medication to the needle for controlling administration of the medication at multiple different computer-controlled depths and medication supply pressures.

20. A needle-point pen apparatus for administering a medication to tissue, the needle-point pen apparatus comprising:

a first oscillating needle having a tip and an elongate shaft;

a second oscillating needle having a tip and an elongate shaft;

a first drive coupled to the first needle and providing a first driving actuation to the first needle, the first driving actuation causing the first needle to reciprocate between one or more extended and retracted positions;

a second drive coupled to the second needle and providing a second driving actuation to the second needle independent of the first drive of the first needle, the second driving actuation causing the second needle to reciprocate between one or more extended and retracted positions;

the first and second needles being designed to at least partially insert the medication into the tissue;

a medication reservoir supplying the medication to the first and second needles; and a computing device including computer executable instructions for controlling the first and second driving actuations to the first and second needles and the supply of the medication to the first and second needles for controlling administration of the medication at multiple different computer-controlled depths and locations of the tissue.

* * * * *